(12) United States Patent
Guichard et al.

(10) Patent No.: US 7,691,899 B2
(45) Date of Patent: Apr. 6, 2010

(54) UREA OLIGOMERS, THE PREPARATION METHOD THEREOF AND PHARMACEUTICAL COMPOSITION CONTAINING SAME

(75) Inventors: Gilles Francois Roger Guichard, Wolfisheim (FR); Jean-Paul Briand, Strasbourg (FR); Vincent Semetey, Aurillac (FR); Patrick Neuberg, Schieren (LU)

(73) Assignee: Centre National de la Recherche Scientifique, Paris (FR)

( * ) Notice: Subject to any disclaimer, the term of this patent is extended or adjusted under 35 U.S.C. 154(b) by 1043 days.

(21) Appl. No.: 10/491,549

(22) PCT Filed: Oct. 2, 2002

(86) PCT No.: PCT/FR02/03355

§ 371 (c)(1),
(2), (4) Date: Oct. 12, 2004

(87) PCT Pub. No.: WO03/029198

PCT Pub. Date: Apr. 10, 2003

(65) Prior Publication Data

US 2005/0038105 A1 Feb. 17, 2005

(30) Foreign Application Priority Data

Oct. 2, 2001 (FR) .................. 01 12659

(51) Int. Cl.
*A01N 43/16* (2006.01)
*A01N 43/10* (2006.01)
*A01N 37/18* (2006.01)

(52) U.S. Cl. .................. 514/453; 514/616; 514/483

(58) Field of Classification Search ................ 514/453, 514/616, 483
See application file for complete search history.

(56) References Cited

U.S. PATENT DOCUMENTS

2002/0143191 A1  10/2002  Guichard et al.

FOREIGN PATENT DOCUMENTS

| DE | 254 319 | 2/1988 |
| WO | 00/42009 | 7/2000 |
| WO | 0042009 | * 7/2000 |

OTHER PUBLICATIONS

Guichard et al., Journal of Organic Chemistry, 1999, 64, 8702-8705.*
Tamilarasu (Bioorganic and Medicinal Chemistry Letters 11, (2001), 505-507).*
Guichard et al (Tetrahedron Letters 41 (2000) 1553-1537).*
Tamilarasu (Journal of American Chemical Society, 1999, 121(7), 1597-1598).*
Wang et al. (Journal of American Chemical Society, 1997, 119(7), 6444-6445).*
Tamilarasu et al.Tetrahedron Letters 41 (200) 1553-1537, p. 506.*
Tamilarasu et al., "Targeting RNA with peptidomimetic oligomers in human cells" Bioorganic & Medicinal Chemistry Letters, Oxford, GB, vol. 11, No. 4, Feb. 26, 2001, pp. 505-507, XP004230046 ISSN: 0960-894X p. 506; figure 1C.

* cited by examiner

*Primary Examiner*—D. Margaret Seaman
*Assistant Examiner*—Nizal S Chandrakumar
(74) *Attorney, Agent, or Firm*—Young & Thompson

(57) ABSTRACT

Compounds having a general formula X-(A)n-Y, wherein: n varies between 6 and 20; X denotes a hydrogen atom, an RaCO, RaOCO, RaNHCO or RaSO2 group, Ra being an alkyl, alkenyl, alkynyl, aryl, aralkyl, heteroaryl group, the groups being substituted or not, on condition that X is different from H when n is equal to 6; A denotes either a group having formula (I) or (II), wherein Ri is a hydrogen atom, an amino acid side chain, an alkyl, alkenyl, alkynyl, aryl, aralkyl or heteroaryl group, said groups being substituted or not, i being an integer of between 1 and n; Y is an NRbRc, Rb and Rc group having the same meaning as given earlier for Ra. The compounds are used for the preparation of medicaments that are intended to treat bacterial, fungal or cytotoxic diseases and, in particular, fungal infections, such as aspergillosis and candidiasis, and resistant bacterial infections.

16 Claims, 5 Drawing Sheets

UREA OLIGOMERS, THE PREPARATION METHOD THEREOF AND PHARMACEUTICAL COMPOSITION CONTAINING SAME

The invention relates to novel urea oligomers, their preparation processes and the pharmaceutical compositions containing them.

The wide functional diversity among the proteins is intimately linked to the extremely sophisticated tertiary and/or quaternary structure of the latter, but it is based on an extremely small set of elementary building blocks, namely the helices, sheets and bends, these structural elements being themselves determined by the amino acid sequence, i.e. by the primary structure of the protein.

Recently, the works of Seebach (Seebach, D.; Matthews, J. L., Chem. Commun., 1997, 2015), of Gellman (Appela, D. H. et al., J. Am. Chem. Soc., 1997, 118, 13071-13072) and of Hannessian (Hanessian, S. et al., J. Am. Chem. Soc., 1998, 120, 8569-8570) have revealed that small oligo-β or γ-peptides (ω-peptides), compounds exclusively of α- or β-amino acids were capable of forming, in solution and in solid phase, unique stable and predictable secondary structures, of helix or sheet type, similar to protein structures. In the reference of Gellman (Gellman, S. H., Acc. Chem. Res., 1998, 31, 173-180), these oligopeptides are called "foldamers".

The resistance of these oligopeptides to proteolysis makes them good and promising candidates in medicinal chemistry for the discovery of novel biological activities and for interfering with the protein-protein recognition process.

To date, very little data exists on the structural and biological properties of enantiopure oligomers not containing any amide function in their skeleton.

An objective of the invention is to provide non-peptide molecules, comprising side chains of amino acids, capable of adopting a helicoidal structure independent of the primary structure of said molecules, i.e. independent of the side chains.

An objective of the invention is to provide molecules capable of adopting a helicoidal conformation and capable of mimicking the active natural helices.

An objective of the invention is also the use of these novel oligomers for the preparation of medicaments the pharmacological properties of which are in particular due to the interaction of these oligomers with the cell membranes.

The invention relates to the use of the compounds of general formula:

$$X\text{-}(A)_n\text{-}Y, \quad (I)$$

in which:
n varies from 6 to 20,
X represents a hydrogen atom, an $R_aCO$, $R_aOCO$, $R_aNHCO$, $R_aSO_2$ or $R_aNHCS$ group,
$R_a$ being fluorescein or a (C1-C10 alkyl), (C1-C10) alkenyl, (C1-C10) alkynyl, (C5-C12) aryl, (C5-C14) aralkyl, (C1-C5) heteroaryl group, said groups being able to be non-substituted or substituted by 1 to 6 substituents chosen from: a halogen atom, an $NO_2$, OH, alkyl (C1-C4), $NH_2$, CN, trihalomethyl, (C1-C4) acyloxy, (C1-C4) dialkylamino, guanidino group, an SH group, a maleimide group,
providing that X is different from H when n is equal to 6,
A represents either:

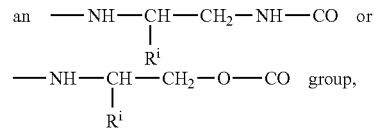

$R^i$ being a hydrogen atom, an amino acid side chain, a (C1-C10) alkyl, (C1-C10) alkenyl, (C1-C10) alkynyl, (C5-C12) aryl, (C5-C14) aralkyl or (C1-C10) heteroaryl group, said groups being able to be non-substituted or substituted by 1 to 6 substituents chosen from: a halogen atom, an $NO_2$, OH, amidine, benzamidine, imidazole, alkoxy, (C1-C4) alkyl, $NH_2$, CN, trihalomethyl, (C1-C4) acyloxy, (C1-C4) dialkylamino, guanidino group, i being an integer comprised from 1 to n, Y is an $NR_bR_c$ group, $R_b$ and $R_c$ having the meaning given previously for $R^i$, for the preparation of medicaments intended for the treatment of bacterial, fungal or cytotoxic diseases.

The invention also relates to the compounds of general formula:

$$X\text{-}(A)_n\text{-}Y, \quad (I)$$

in which:
n varies from 6 to 20,
X represents a hydrogen atom, an $R_aCO$, $R_aOCO$, $R_aNHCO$, $R_aSO_2$ or $R_aNHCS$ group,
$R_a$ being fluorescein or a (C1-C10) alkyl, (C1-C10) alkenyl, (C1-C10) alkynyl, (C5-C12) aryl, (C5-C14) aralkyl, (C1-C5) heteroaryl group, said groups being able to be non-substituted or substituted by 1 to 6 substituents chosen from: a halogen atom, an $NO_2$, OH, (C1-C4) alkyl, $NH_2$, CN, trihalomethyl, (C1-C4) acyloxy, (C1-C4) dialkylamino, guanidino group, an SH group, a maleimide group,
providing that X is different from H when n is equal to 6,
A represents either:

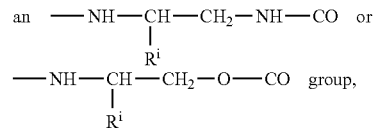

$R^i$ being a hydrogen atom, an amino acid side chain, a (C1-C10) alkyl, (C1-C10) alkenyl, (C1-C10) alkynyl, (C5-C12) aryl, (C5-C14) aralkyl or (C1-C10) heteroaryl group, said groups being able to be non-substituted or substituted by 1 to 6 substituents chosen from: a halogen atom, an $NO_2$, OH, amidine, benzamidine, imidazole, alkoxy, (C1-C4) alkyl, $NH_2$, CN, trihalomethyl, (C1-C4) acyloxy, (C1-C4) dialkylamino, guanidino group, i being an integer comprised from 1 to n, Y is a $NR_bR_c$ group, $R_b$ and $R_c$ having the meaning given previously for $R^i$, providing that the compounds corresponding to the following formulae are excluded:

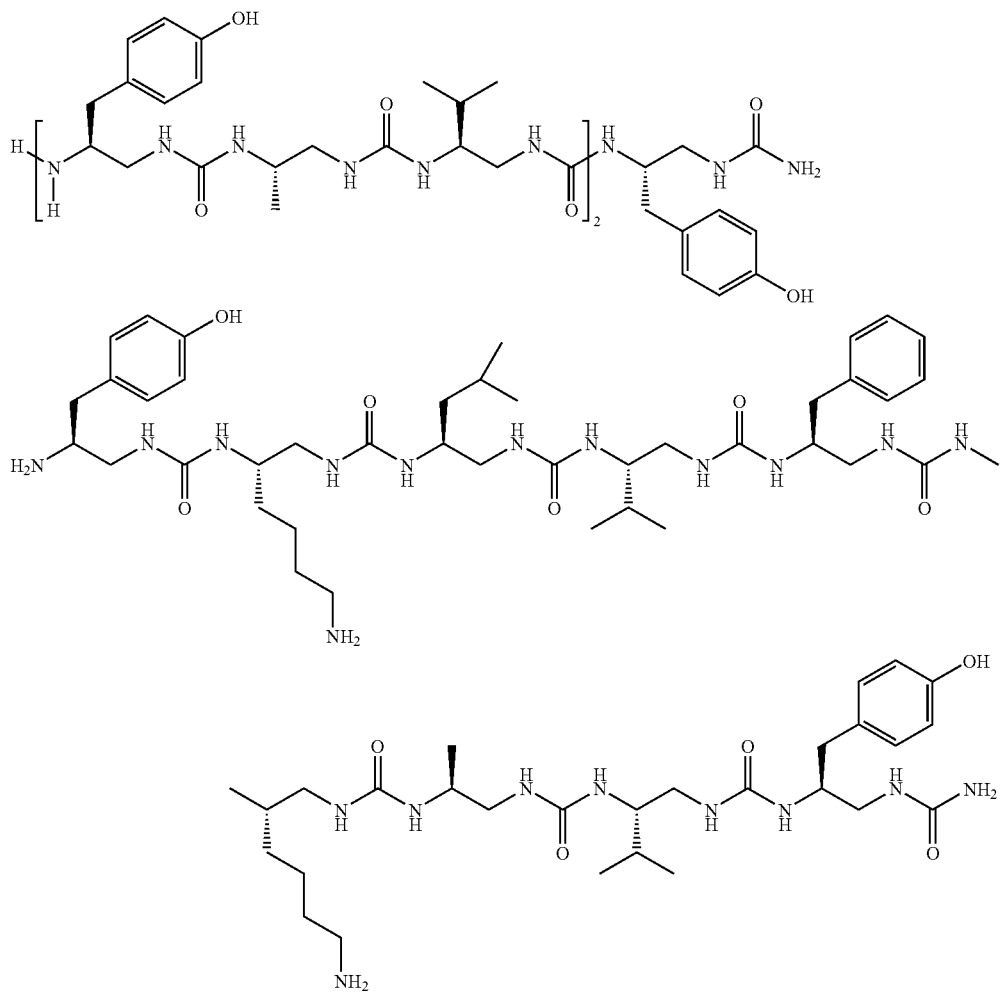

The expression "A represents either an

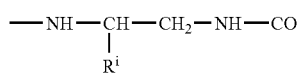

or

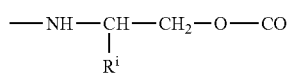

group" means that the A group, in the $(A)_n$ chain, is in a random manner, one of the groups defined above.

The invention relates to the compounds as defined above, characterized in that n is equal to 6, 7, 8 or 9, and corresponding to the following formulae:

| | |
|---|---|
| $X-A^3-A^2-A^3-A^2-A^2-A^3-A^2-Y$ | (13) |
| $X-A^2-A^3-A^2-A^2-A^3-A^2-Y$ | (14) |
| $X-A^3-A^2-A^3-A^3-A^2-A^3-A^2-Y$ | (15) |
| $X-A^3-A^2-A^3-A^2-A^2-A^3-A^2-Y$ | (16) |
| $X-A^2-A^3-A^2-A^2-A^3-A^2-A^3-Y$ | (17) |
| $X-A^2-A^3-A^2-A^3-A^3-A^2-A^3-Y$ | (18) |
| $X-A^3-A^2-A^3-A^2-A^2-A^3-A^2-A^3-Y$ | (19) |
| $X-A^2-A^3-A^2-A^3-A^3-A^2-A^3-A^2-Y$ | (20) |
| $X-A^1-A^2-A^3-A^3-A^1-A^2-A^3-A^1-A^3-Y$ | (1) |
| $X-A^1-A^2-A^3-A^3-A^1-A^2-A^3-A^3-A^1-Y$ | (2) |
| $X-A^1-A^2-A^3-A^3-A^1-A^3-A^2-A^1-A^3-Y$ | (3) |
| $X-A^1-A^2-A^3-A^3-A^2-A^1-A^3-A^1-A^3-Y$ | (4) |
| $X-A^1-A^2-A^3-A^2-A^1-A^3-A^3-A^1-A^3-Y$ | (5) |
| $X-A^1-A^2-A^3-A^3-A^2-A^1-A^3-A^2-A^3-Y$ | (6) |
| $X-A^1-A^2-A^3-A^1-A^2-A^3-A^1-A^2-A^3-Y$ | (7) |
| $X-A^2-A^1-A^3-A^2-A^1-A^3-A^2-A^1-A^3-Y$ | (8) |
| $X-A^1-A^2-A^3-A^2-A^3-A^3-A^2-A^1-Y$ | (9) |

$$X\text{-}A^1\text{-}A^3\text{-}A^2\text{-}A^3\text{-}A^2\text{-}A^3\text{-}A^2\text{-}A^3\text{-}A^1\text{-}Y \quad (10)$$

$$X\text{-}A^1\text{-}A^2\text{-}A^3\text{-}A^2\text{-}A^1\text{-}A^2\text{-}A^3\text{-}A^2\text{-}A^1\text{-}Y \quad (11)$$

$$X\text{-}A^3\text{-}A^2\text{-}A^3\text{-}A^2\text{-}A^2\text{-}A^3\text{-}A^2\text{-}A^3\text{-}A^3\text{-}Y \quad (12)$$

in which:

X and Y are as defined above, $A^1$ corresponds to the A group as defined above, in which $R^i$ represents an aromatic side chain, such as a benzyl group corresponding to the phenylalanine side chain, a 4-hydroxybenzyl group corresponding to the tyrosine side chain or a (3-indolyl)methyl group corresponding to the tryptophane side chain, $A^2$ corresponds to the A group as defined above, in which $R^i$ represents a basic chain corresponding to lysine ($—(CH_2)_4—NH_2$), arginine ($—(CH_2)_3NH—C(=NH)NH_2$) or ornithine ($—(CH_2)_3\text{-}NH_2$), or a (C1-C10) alkyl, (C1-C10) alkenyl, (C1-C10) alkynyl group, said groups being able to be non-substituted or substituted by 1 to 6 substituents chosen from: an amidine, $NH_2$, guanidino group, $A^3$ corresponds to the A group as defined above, in which $R^i$ represents a hydrophobic side chain of methyl type corresponding to the alanine side chain, isopropyl corresponding to the valine side chain, isobutyl corresponding to the leucine side chain and sec-butyl corresponding to the isoleucine side chain.

Advantageous compounds according to the invention are compounds as defined above, corresponding to the following formulae:

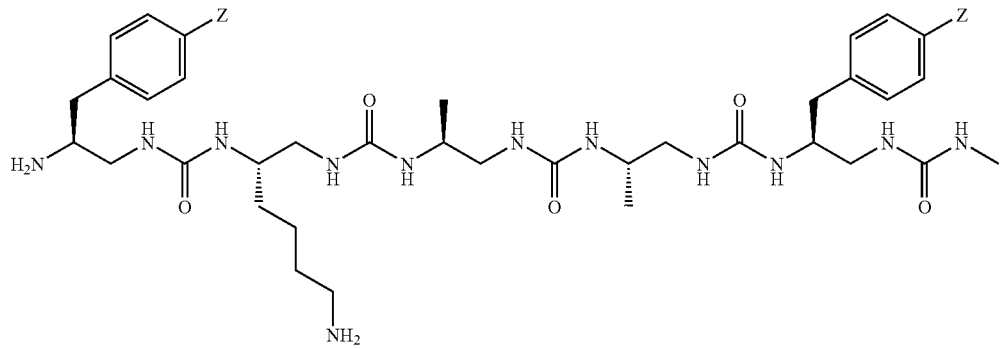

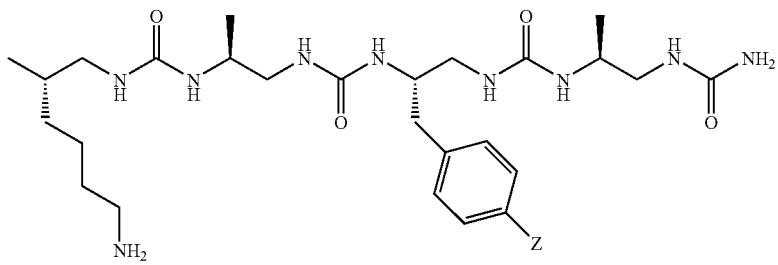

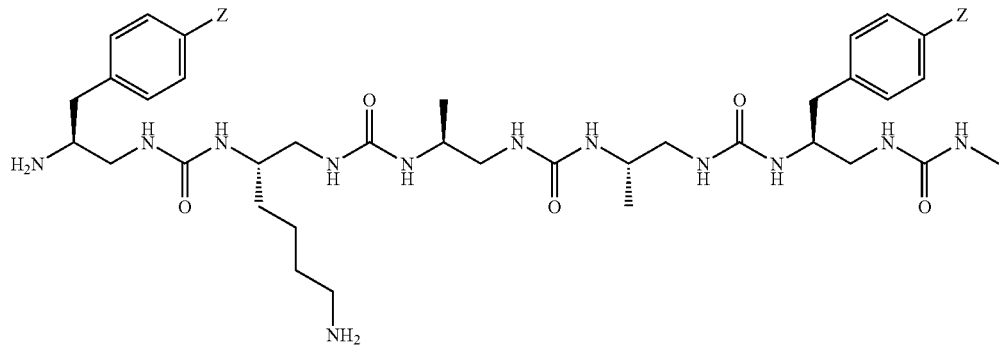

-continued
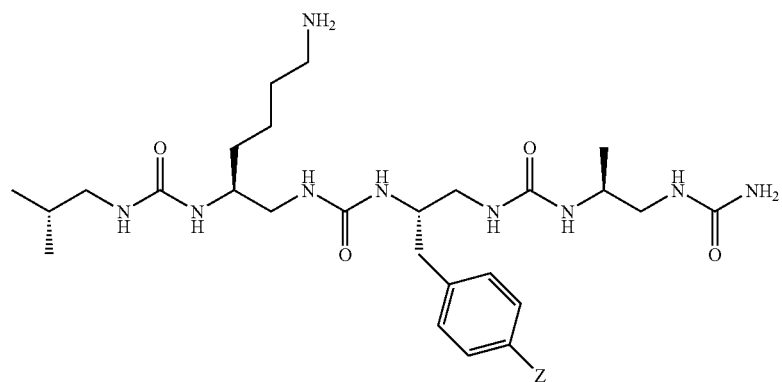
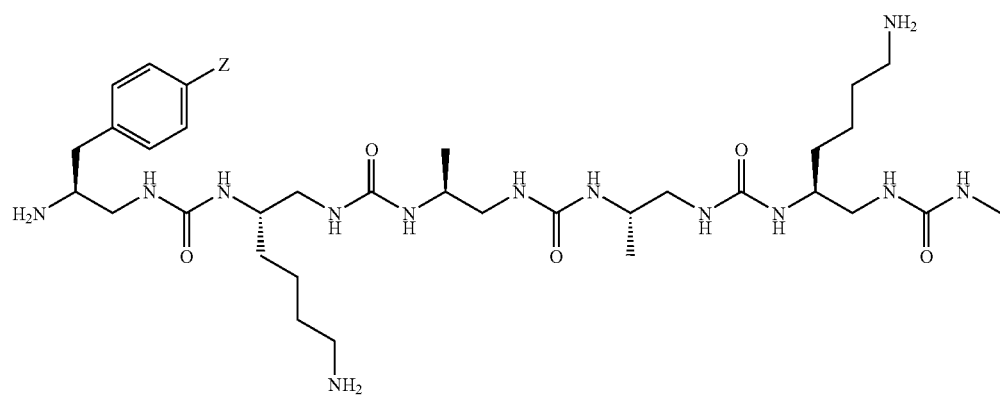
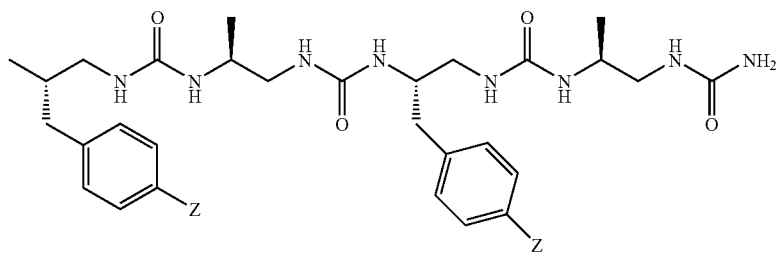
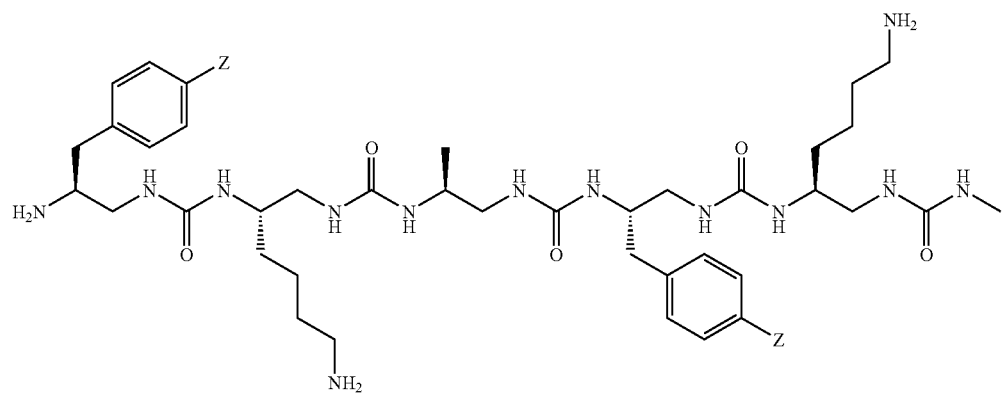

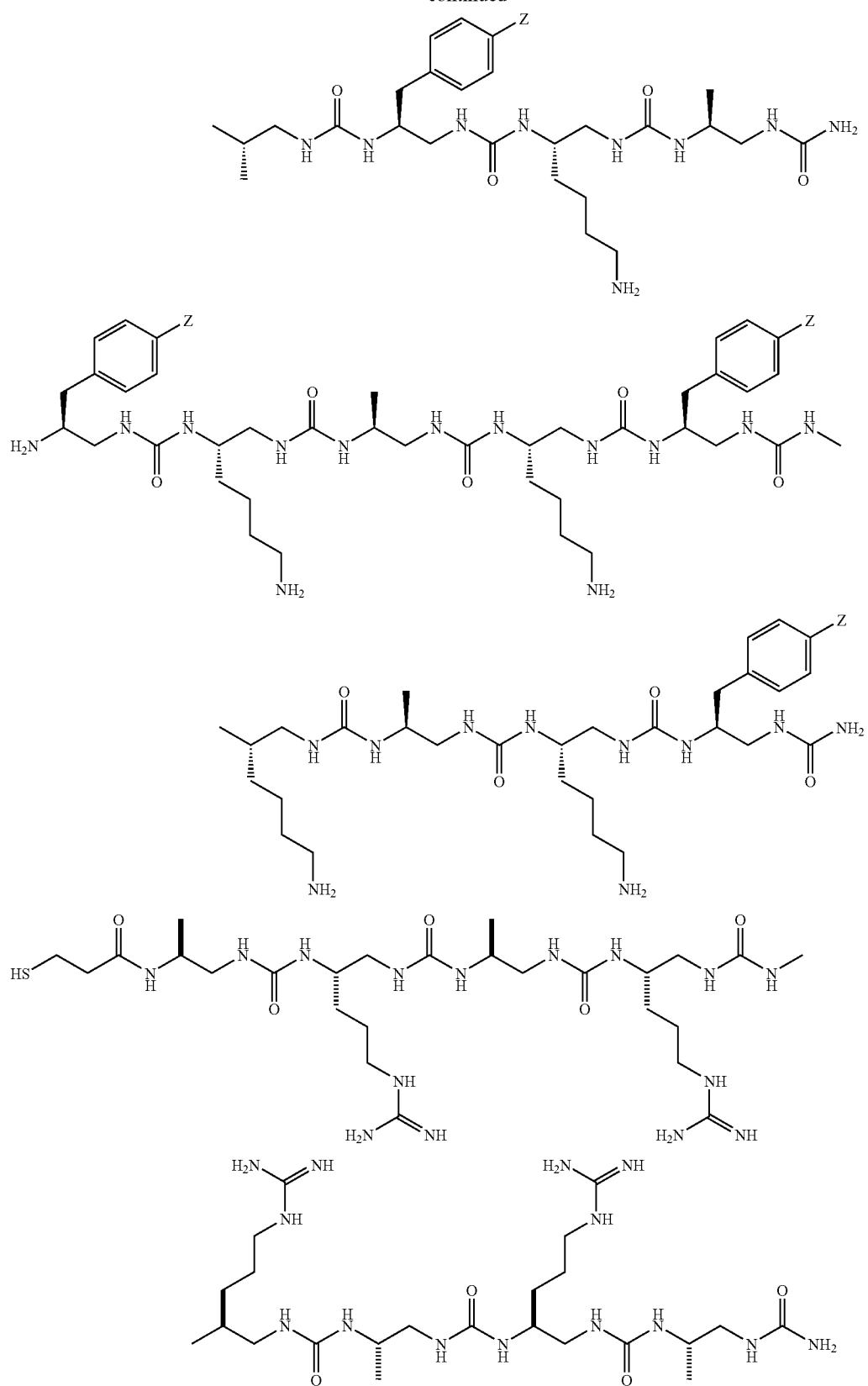

-continued
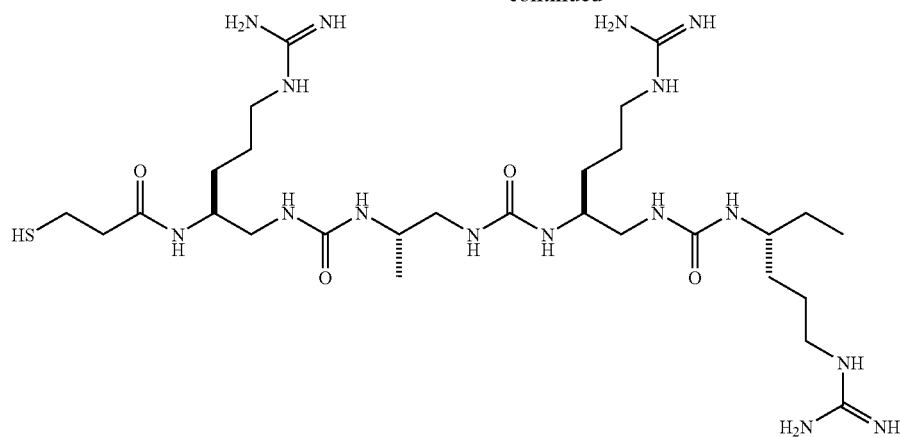
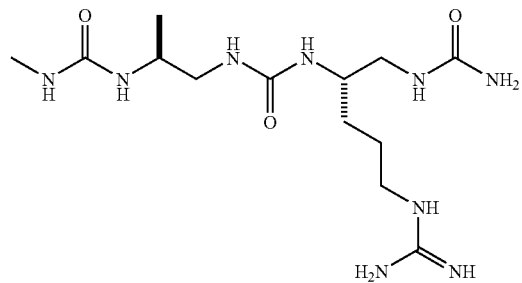
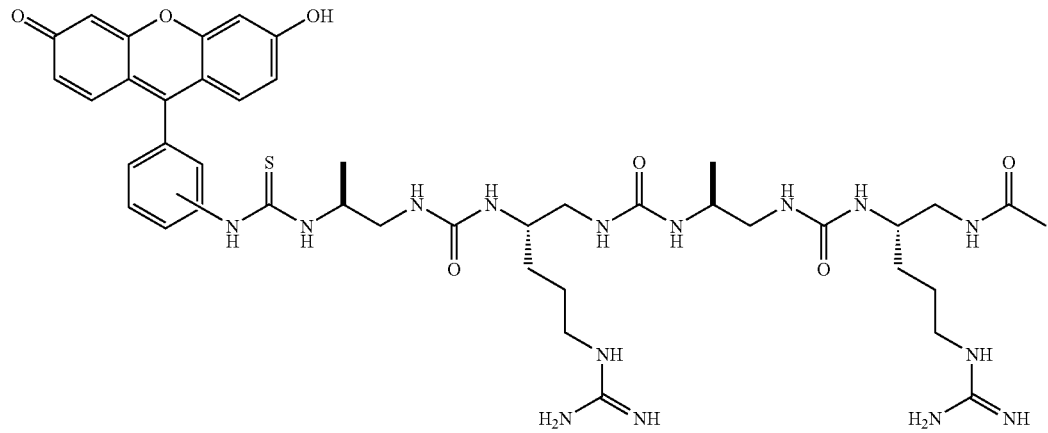
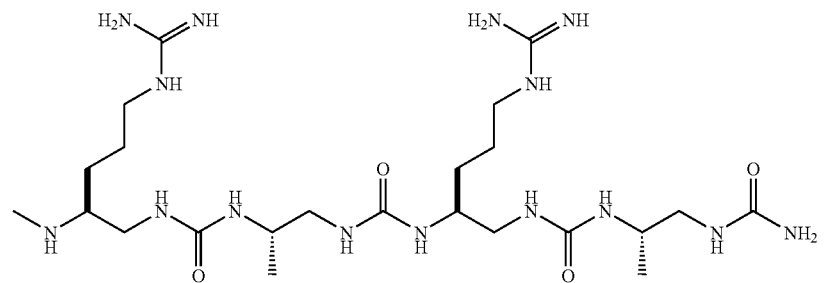

-continued

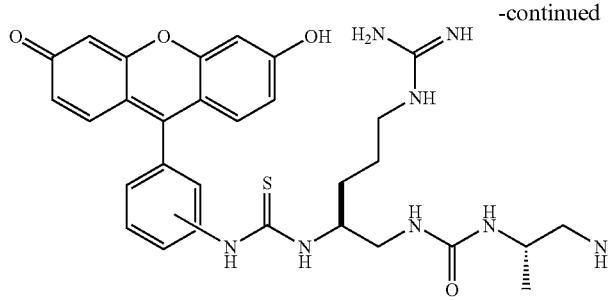
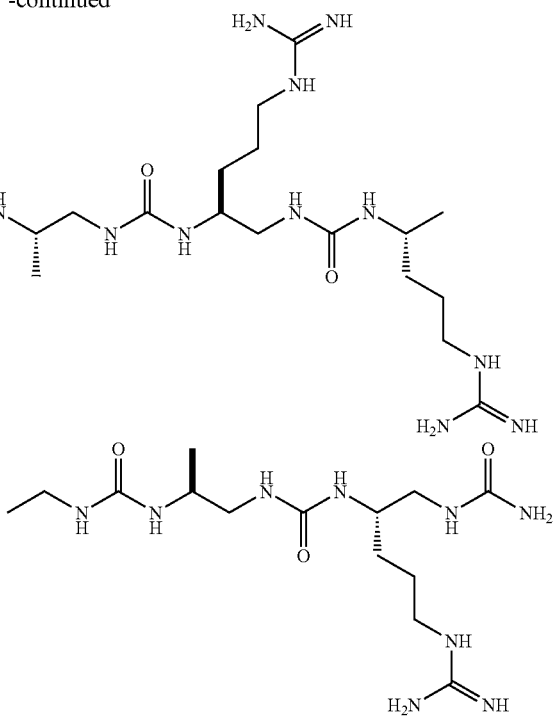
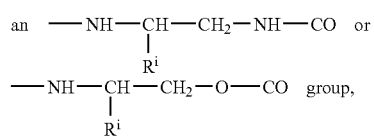

in which Z represents either a hydrogen atom or an OH group.

The invention also relates to the compounds as defined above, characterized in that at least approximately 10%, advantageously approximately 10% to approximately 50% of the $R^i$ substituents are amino acid side chains of basic character.

The expression "amino acid side chains of basic character" designates chains comprising at least one or more groups having the possibility of accepting a proton, according to the Bronsted definition. For example, these groups can be (primary, secondary or tertiary) amines, amides, amidines, benzamidines, guanidines, imidazoles, imidazolines or pyridines.

Advantageous compounds of the invention are compounds as defined above, characterized in that the amino acid side chains of basic character contain primary, secondary or tertiary amine groups, imidazole, guanidine, amidine or benzamidine groups.

The molecules carrying the abovementioned side chains, to the exclusion of any aspartate or glutamate-type negatively charged chain, are cationic and are therefore electrostatically attracted by the negatively charged microbial surfaces. In the case of Gram−bacteria, the molecules can initially interact with the wall rich in lipopolysaccharide (LPS) of the outer membrane. In the case of the Gram+bacteria, the surface is negatively charged due to the presence of teichoic and teichuronic acids and carboxyl groups of the amino acid residues in the peptidoglycanes. Once the cytoplasmic membrane is reached, the cationic molecules can then interact with the negatively charged heads of the phospholipids of the outer wall (Tossi et al., Biopolymers, 2000, 55, 4-30).

The invention relates to the compounds possessing a helical structure and corresponding to the following general formula:

$$X\text{-}(A)_n\text{-}Y, \qquad (I)$$

in which:

n varies from 6 to 20,

X represents a hydrogen atom, a $R_aCO$, $R_aOCO$, $R_aNHCO$, $R_aSO_2$ or $R_aNHCS$ group, $R_a$ being a (C1-C10) alkyl, (C1-C10) alkenyl, (C1-C10) alkynyl, (C5-C12) aryl, (C5-C14) aralkyl, (C1-C5) heteroaryl group, said groups being able to be non-substituted or substituted by 1 to 6 substituents chosen from: a halogen atom, an $NO_2$, OH, (C1-C4) alkyl, $NH_2$, CN, trihalomethyl, (C1-C4) acyloxy, (C1-C4) dialkylamino, guanidino group, an SH group, a maleimide group, fluorescein, providing that X is different from H when n is equal to 6, A represents either:

an —NH—CH(R$^i$)—CH$_2$—NH—CO or
—NH—CH(R$^i$)—CH$_2$—O—CO group, $R^i$ being a hydrogen atom, an amino acid side chain, a (C1-C10) alkyl, (C1-C10) alkenyl, (C1-C10) alkynyl, (C5-C12) aryl, (C5-C14) aralkyl or (C1-C10) heteroaryl group, said groups being able to be non-substituted or substituted by 1 to 6 substituents chosen from: a halogen atom, an $NO_2$, OH, amidine, benzamidine, imidazole, alkoxy, (C1-C4) alkyl, $NH_2$, CN, trihalomethyl, (C1-C4) acyloxy, (C1-C4) dialkylamino, guanidino group, i being an integer comprised from 1 to n, Y is a $NR_bR$ group, $R_b$ and $R_c$ having the meaning given previously for $R^i$, said helix having the following characteristics:

it has a regular pitch to the right, comprised from approximately 4.9 Å to approximately 5.3 Å, and in particular equal to approximately 5 Å, it comprises from 2.4 to 2.6 residues per turn and in particular 2.5 residues per turn, its internal diameter calculated from the centres of the atoms is comprised from approximately 3.8 Å to approximately 4.6 Å, and in particular equal to approximately 4.2 Å, its internal diameter calculated from the Van der Waals surface is comprised from approximately 1.4 Å to approximately 1.8 Å, and in particular equal to approximately 1.6 Å, By "residue", is designated the A group as defined above.

The expression "internal diameter calculated from the centres of the atoms" signifies that, in a regular part of the structure, modeled from the data obtained by nuclear magnetic resonance, it is possible to define a diameter between two diametrically opposed atoms, knowing the axis of the helix. The distance obtained is then measured from the centre of the atoms.

The expression "internal diameter calculated from the Van der Waals surface" signifies that, in a regular part of the structure, it is possible to define, knowing the axis of the helix, a diameter between two diametrically opposed selected atoms. The distance obtained is then the previously calculated distance, from which the van der Waals radii of the two atoms selected have been subtracted. By way of example, the van der Waals radii of the following atoms can be given: 1.2 Å for the hydrogen atom; 1.5 Å for the oxygen atom; 1.6 Å for the nitrogen atom; 1.7 Å for the carbon atom and 1.8 Å for the sulfur atom.

It is noted that the helical structure of the compounds of the invention results in part from the existence of two hydrogen bonds between the oxygen atom of the CO group of the i residue and the two hydrogen atoms of the NH groups of the i+3 residue and N'H of the i+2 residue respectively. For greater clarity, the nitrogen atom situated between the $CH_2$ group and the CO group is represented by N'.

These hydrogen bonds, between, on the one hand, the oxygen atom of the CO group of the i residue and the hydrogen atom of the NH group of the i+3 residue, and, on the other hand, between the oxygen atom of the CO group of the i residue and the hydrogen atom of the N'H group of the i+2 residue, lead to the formation of rings with 12 or 14 atoms. In fact, the hydrogen bond between the CO group of the i residue and the hydrogen atom of the NH group of the i+3 residue closes a 14-atom ring whereas the hydrogen bond between the CO group of the i residue and the hydrogen atom of the N' group of the i+2 residue closes a 12-atom ring.

It is possible to correlate the helical structure observed by NMR in methanol and in pyridine with a characteristic signal in circular dichroism (CD).

Circular dichroism represents a considerable source of information on the structure of biological macromolecules such as proteins or DNA (G. D. Fasman, Circular Dichroism and the conformational analysis of biomolecules, Plenum press, NY, 1996). Circular Dichroism is the measurement as a function of wavelength of the ability of an optically active molecule to absorb in different manner the two constituents (turning to the left (El) and turning to the right (Er) of a polarized light beam. The optical activity is therefore linked to the optical anisotropy of the medium studied. The combination of the differential absorption (circular dichroism) and the difference in speed of transmission of the left and right polarized light (optical activity) in the spectral region where an optically active absorption band is manifested is called the Cotton effect (Pierre Crabbe, Applications de la dispersion rotatoire optique et du dichroïsme circulaire optique en chimie organic, Gauthier-Villars, Paris, 1968).

In methanol, an intense Cotton effect is observed which probably corresponds to the helicoidal form (maximum 205 nm) for the heptamer and for the nanomer in methanol and an absence of signal for shorter oligomers: a hexamer the residue 1 of which is not acylated (absence of carbonyl group being able to be engaged in a hydrogen bond with the residue 3) gives almost no signal at this wavelength. In the case of the heptamer, the study of the signal at 205 nm as a function of temperature indicates that the latter is not very sensitive to an increase in temperature and suggests that the secondary structure persists up to 60° C. and that the unfolding mechanism is non-cooperative (a straight line with a negative gradient is obtained). By heating a compound, the structure is destabilized little by little and the complete denaturation of the molecule probably passes through a large number of partially folded intermediates states: this is then referred to as non-cooperative effect.

In trifluoroethanol, the characteristic signal disappears whereas in water a part of the signal at 205 nm remains, which suggests that the helical structure is in part present in the water.

It has also been noted that a minimum of six residues was necessary in order to obtain a helical compound. However, in the case of six residues (n=6), it is advantageous or even necessary to protect the NH terminal group by an acyl group in order to stabilize the structure of the helix.

The term "compounds possessing a helical structure" designates both compounds the helicoidal structure of which is total and compounds of which the helicoidal structure is partial.

A partial helicoidal structure is defined when either only part of the molecule adopts the structural characteristics of the helix, or when a dynamic equilibrium exists between the helicoidal form and other conformational states. This can be observed by different techniques which include NMR in solution or circular dichroism. The stability of the helix can also be measured by thermal studies.

The invention also relates to the compounds as defined above and corresponding to one of the following formulae:

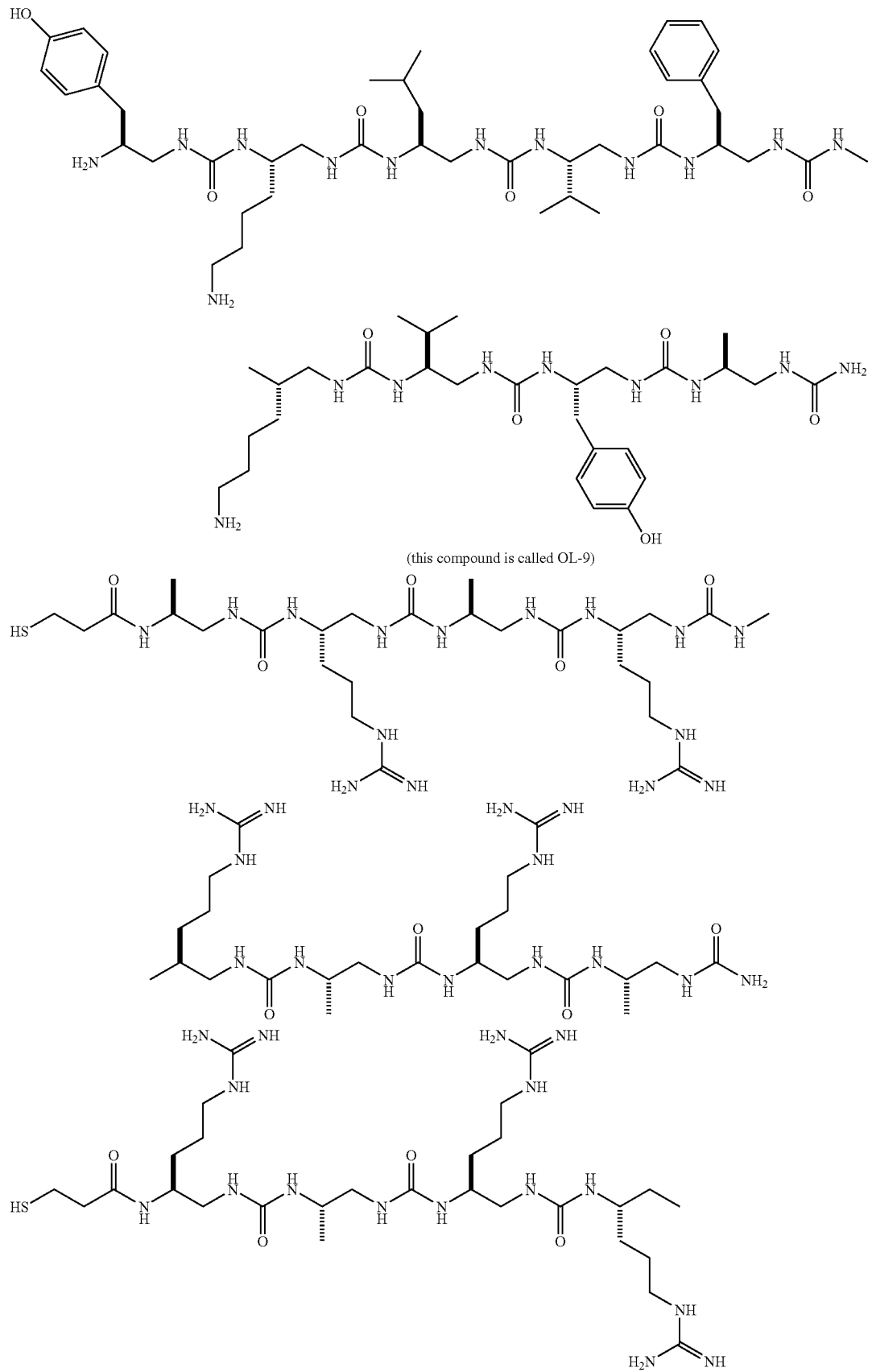
(this compound is called OL-9)

-continued
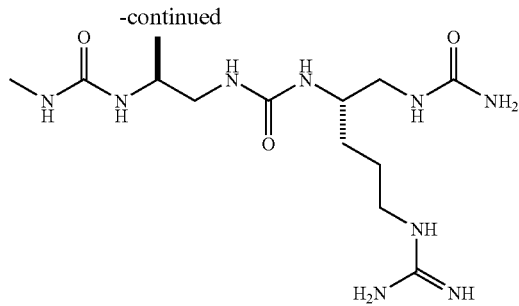
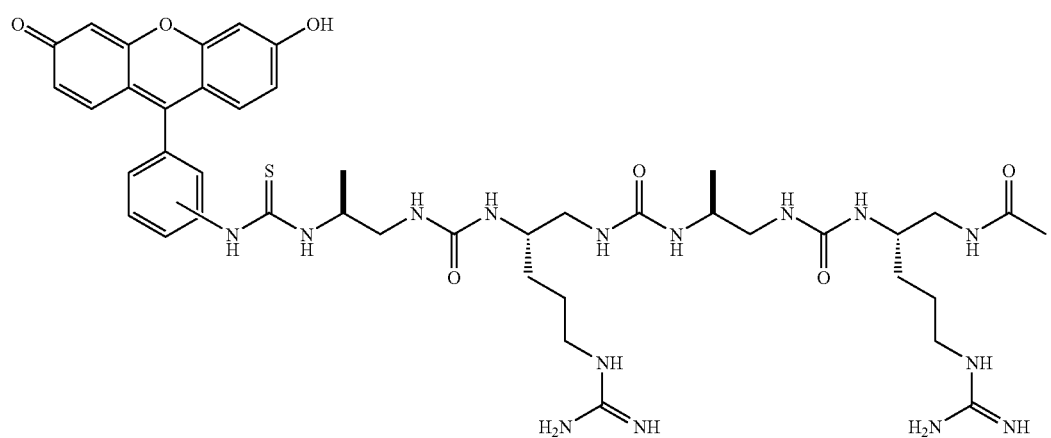
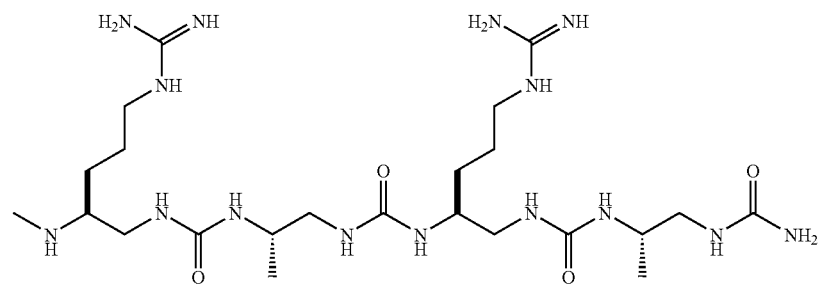

-continued

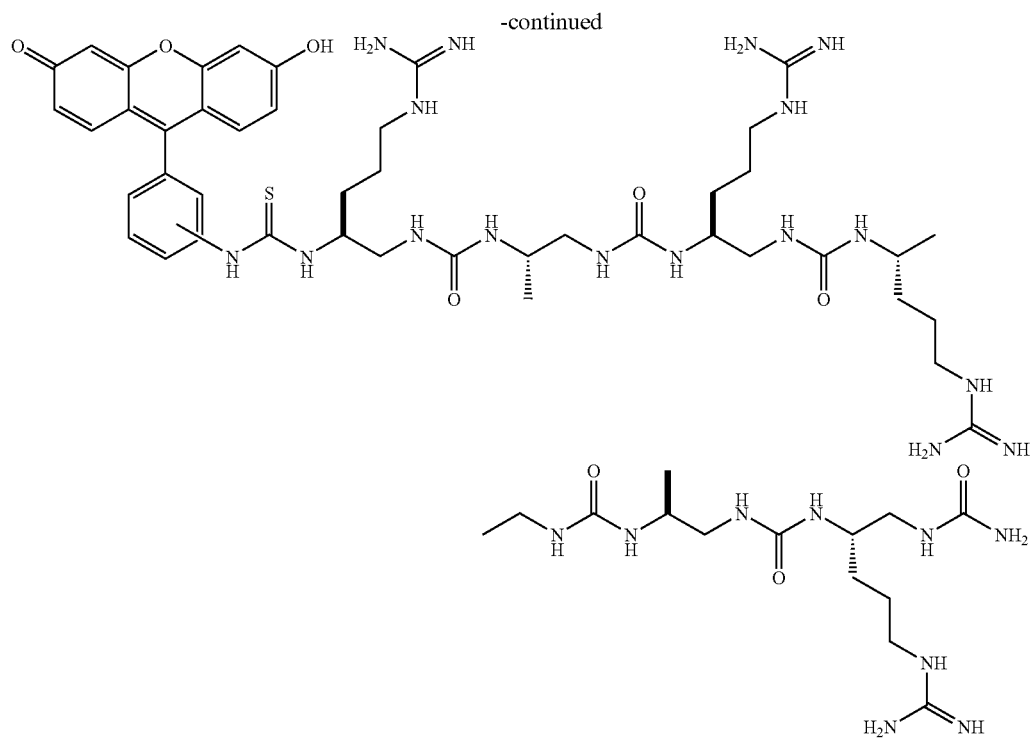

The invention also relates to a composition containing at least one compound as defined above and at least one solvent, said solvent having the property of conferring on the molecules of said compound a helicoidal form, even partially, in the case of a conformational equilibrium between the molecules of said compound in the helicoidal form and the molecules of said compound in the non-helicoidal form, and being in particular chosen from alcohols, pyridine, acetonitrile, dimethylsulphoxide, water in the presence or absence of micelles or of lipids, and being advantageously chosen from water in the presence or absence of micelles, methanol, ethanol, isopropanol, trifluoroethanol, hexafluoroisopropanol, dimethylsulphoxide or any mixture of these solvents.

The structure is extremely stable and well-defined in pyridine or methanol. In water, the measurements carried out by circular dichroism suggest that the helicoidal structure can be partial as the signal at 205 nm is less intense than in methanol. However, the structure can also be measured by thermal studies.

The invention also relates to a process for preparing in solid phase compounds of formula (I) as defined above, from pre-activated monomers of formula GP-A-W, in which:

GP is a protective group chosen from Fmoc, Teoc, phthalimide, Alloc, BOC and Cbz, A is as defined above, W originates from the W—H group chosen from: N-hydroxysuccinimide, phenol, pentafluorophenol, pentachlorophenol, p-nitrophenol, 2,4-dinitrophenol, 2,4,5-trichlorophenol, 2,4-dichloro-6-nitrophenol, hydroxy-1,2,3-benzotriazole, 1-oxo-2-hydroxydihydrobenzotriazine (HODhbt), 7-aza-1-hydroxy-benzotriazole (HOAt), 4-aza-1-hydroxybenzo-triazole (4-HOAt), imidazole, tetrazole, and WANG resin, and is preferably N-hydroxysuccinimide or p-nitrophenol, characterized in that it comprises the following stages:

a) a GP-A-W coupling stage as defined above on the amine function of a support, said stage allowing the grafting of the-A-GP group to said amine function of said support, b) a stage of cleavage of the GP group under appropriate conditions, c) the sequential repetition of stages a) and b) until n A groups have been grafted to said support, d) a stage of introduction of the $R_aCO$, $R_aOCO$, $R_aNHCO$ or $R_aSO_2$ groups, $R_a$ being as defined above, e) a stage of cleavage of the compound of formula (I) from the support by appropriate means, which allows the removal of the resin and the release of the Y group, as defined above.

By "pre-activated monomer", is designated a carbamic acid or carbonic acid derivative capable of reacting with primary or secondary amines, in the presence or absence of a base in an organic solvent and generally at ambient temperature, in order to produce respectively a urea or a carbamate.

It should be recalled that the protective groups: Fmoc, Teoc, Alloc, BOC and Cbz groups correspond respectively to the fluorenylmethoxycarbonyl, trimethylsilyl-ethyloxycarbonyl, allyloxycarbonyl, tert-butyloxycarbonyl and benzyloxycarbonyl groups.

The coupling stage of the abovementioned preparation process in solid phase is carried out in organic medium (DMF, THF, $CH_2Cl_2$, NMP), by adding a solution of the preactivated monomer (1 to 20 equivalents relative to the quantity of free amine on the resin), in the presence or absence of a catalyst, such as hydroxybenzotriazole, to a suspension of resin in the solvent. This stage can be followed or not followed by the addition of an organic base (DIEA, NMM, pyridine, $Et_3N$, collidine, lutidine etc.).

The cleavage stage is chosen as a function of the protective group GP. In the case of the Fmoc group, the latter can be deprotected by a 20% solution of piperidine in DMF. In the case of the Teoc group, the latter can be deprotected by a solution of tetrabutylammonium fluoride in THF. These techniques are standard and are mostly described in: "Protecting Groups" by P. J. Kocienski (Editions Thieme).

The oligomer is then elongated by repetition of the coupling and cleavage stages, up to the last residue A of the sequence.

After deprotection of the last GP group, the $R_aCO$, $R_aOCO$, $R_aNHCO$ or $R_aSO_2$ groups can be introduced, if appropriate, by reaction of the amine on the resin with for example an acyl chloride ($R_aCOCl$), a mixed anhydride ($R_aOCOOR_a$), an isocyanate ($R_aNCO$) or a sulphanyl chloride ($R_aSO_2Cl$) under standard conditions.

The cleavage stage can be carried out by treatment of the resin in acid medium by well-known mixtures used for peptide synthesis, such as a TFA/$H_2O$/triisopropylsilane mixture (9.5/2.5/2.5).

An advantageous preparation process according to the invention is a preparation process as defined above, characterized in that stage a) can be carried out in the presence or absence of a tertiary base such as DIEA, collidine, NMM or lutidine, and in the presence or absence of a catalyst such as HOBt.

By definition, DIEA designates diisopropylethylamine, NMM designates N-methylmorpholine and HOBt 1-hydroxybenzotriazole.

The invention also relates to the preparation process as defined above, characterized in that stage a) can be carried out in a solvent such as the DMF, $CH_2Cl_2$, THF or N-methylpyrrolidone.

An advantageous preparation process according to the invention is a preparation process as defined above, characterized in that the GP group is an Fmoc group.

The invention also relates to a preparation process in phase liquid of the compounds of formula (I) as defined above, from pre-activated monomers of formula GP-A-W, in which:

GP is a protective group chosen from Fmoc, Alloc, BOC and Cbz,

A is as defined above,

W originates from the W—H group chosen from: N-hydroxysuccinimide, phenol, pentafluorophenol, pentachlorophenol, p-nitrophenol, 2,4-dinitrophenol, 2,4,5-trichlorophenol, 2,4-dichloro-6-nitrophenol, hydroxy-1,2,3-benzotriazole, 1-oxo-2-hydroxydihydrobenzotriazine (HODhbt), 7-aza-1-hydroxy-benzotriazole (HOAt), 4-aza-1-hydroxybenzo-triazole (4-HOAt), imidazole and tetrazole, and is preferably N-hydroxysuccinimide or p-nitrophenol, characterized in that it comprises the following stages:

a) a stage of coupling of GP-A-W as defined above to the amine function of the A group of the H-A-Y derivative, b) a stage of cleavage of the GP group under appropriate conditions, c) the sequential repetition of stages a) and b) until n A groups have been grafted to the amine function mentioned above, d) a stage of introduction of the $R_aCO$, $R_aOCO$, $R_aNHCO$ or $R_aSO_2$ groups, $R_a$ being as defined above, e) a cleavage stage of the compound of formula (I) by appropriate means.

The coupling stage of the abovementioned preparation process in liquid phase is carried out in organic medium (DMF, THF, $CH_2Cl_2$, NMP), by adding a solution of the preactivated monomer (1 to 1.5 equivalents relative to the quantity of primary or secondary amine of the starting H-A-Y derivative). This stage can be followed or not followed by the addition of an organic base (DIEA, NMM, pyridine, $Et_3N$, collidine, lutidine etc.). This stage is followed by thin-layer chromatography. At the end of the reaction, a saturated solution of sodium hydrogen carbonate is added, then dichloromethane for example. The organic phase is washed with a saturated solution of sodium hydrogen carbonate then with a saturated solution of NaCl. The organic phase can optionally be washed in acid medium (1N HCl or IN $KHSO_4$). The organic phase is recovered, dried over $MgSO_4$ and the solvent is evaporated off in order to produce the expected compound. If the crude product contains impurities, it can be purified by chromatography on silica with an appropriate solvent system.

The cleavage stage corresponds to the deprotection of the GP protective group. In the case of the BOC group, the latter can be deprotected by TFA. In the case of the Teoc group, the latter can be deprotected by a solution of tetrabutylammonium fluoride in THF. These techniques are standard and are mostly described in "Protecting Groups" of P. J. Kocienski (Editions Thieme).

The oligomer is then elongated by repetition of the coupling and cleavage stages, up to the last residue A of the sequence.

After the deprotection of the last GP group, the $R_aCO$, $R_aOCO$, $R_aNHCO$ or $R_aSO_2$ groups can be introduced, if appropriate, by reaction of the deprotected amine with for example an acyl chloride ($R_aCOCl$), a mixed anhydride ($R_aOCOOR_a$), an isocyanate ($R_aNCO$) or a sulphanyl chloride ($R_aSO_2Cl$) under standard conditions. The final compound can be purified by chromatography on silica (normal phase or reversed phase).

The invention also relates to a process for the preparation of the compounds as defined above, by bringing one of the compounds as defined above or one of the compounds of formula (VIIc) or (VIId), into contact with a solvent such as methanol, ethanol, trifluoroethanol, hexafluoroisopropanol, water, or with biological buffers, such as saline or non-saline phosphate buffers, or with a micelle or lipid medium.

The compounds of formula (VIIc) are compounds called OL-7, which correspond to the following formula:

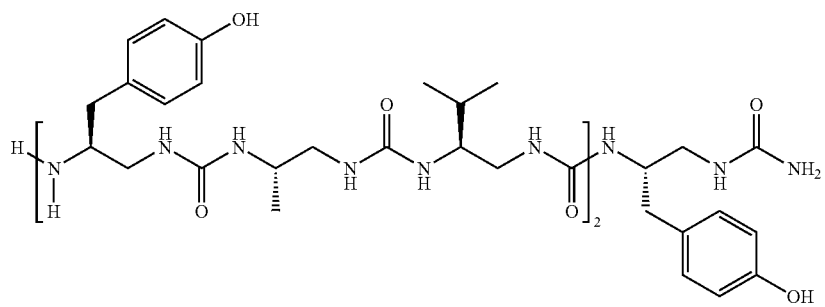

The compounds of formula (VIId) are compounds corresponding to the following formula:

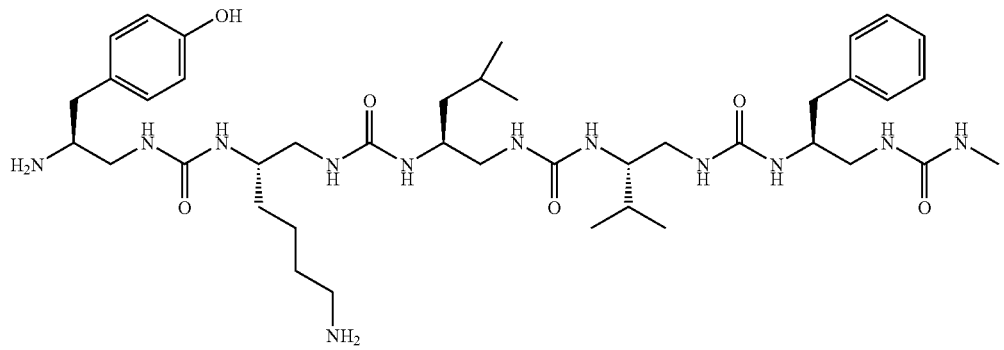

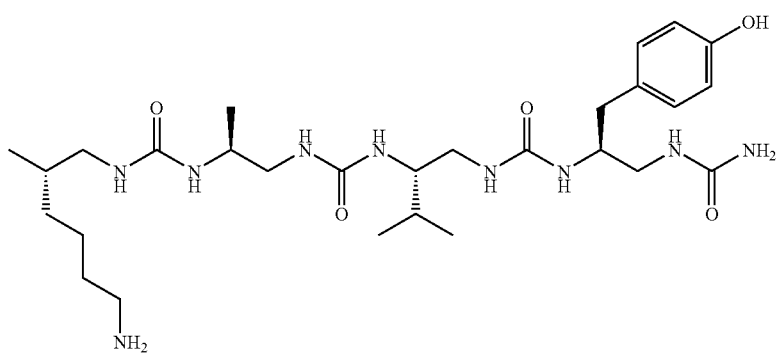

The invention relates to the use of the compounds as defined above for the preparation of medicaments intended for the treatment of bacterial, fungal or cytotoxic diseases, and in particular of fungal infections such as *aspergillosis* and *candidosis*, and of resistant bacterial infections.

By "bacterial diseases", is meant the emergent infections associated with the following bacteria:

*Legionella*, bacterium associated with legionellosis,

*Escherichia coli* O157:H7: discovered in 1982, this bacterium which is normally transmitted by means of contaminated food, has been at the origin of attacks of hemolytic and uremic syndromes,

*Borrelia burgdorferi*: detected in the United States in 1982, it has been identified as being the cause of Lyme's disease,

*Vibrio cholerae* O139: new strain associated with an epidemic cholera,

*Helicobacter pyroli*: bacterium associated with a gastrointestinal ulcer.

The infections associated with bacteria which are becoming resistant to more and more extensive range of antibiotics are also designated. Thus, in numerous regions, the antibiotics of first intention, which are inexpensive, have lost their effectiveness against the infections linked to the following bacteria: *Escherichia coli, Streptococcus pneumoniae, Enterococcus faccalis, Mycobacterium tuberculosis, Pseudomonas aeruginosa, Neisseria gonorrhoca, Pneumococcus, Shigella, Staphylococcus aureus* (associated with a staphylococcic toxic shock) and *Moraxella catarrhalis*.

By "fungal diseases", is designated the infections caused by the following pathogenic fungi: *Candida albicans*, associated with candidosis, *Aspergillus nidulans, Aspergillus parasiticus*, associated with aspergillosis, and *Neurospora crassa*.

The fungal diseases include the diseases caused by pathogenic fungi, in particular those of the family of fungi imperfecti, in particular the moniliales or also those of the family of the hyprocreales or of that of the sphaeriales.

By "cytotoxic diseases", is designated in particular cancers, and in particular tumors of the digestive system (liver, intestine, oesophagus, pancreas etc.), the urogenital system (uterus, prostate, kidney, bladder etc.), the endocrine glands, the eye, the skin, the breast, the bone, the nervous system, the thorax (lung etc.).

The invention relates to a pharmaceutical composition characterized in that it comprises, as active ingredient at least one of the compounds as defined above, in combination with a pharmaceutically acceptable vector.

An advantageous pharmaceutical composition according to the invention is a pharmaceutical composition as defined above, characterized in that it contains per unit dose from 10 to 2000 mg of one of the compounds as defined above.

The pharmaceutical compositions according to the invention can be administered by oral, parenteral, rectal or topical route.

As solid compositions for oral administration tablets, pills, powders (in particular in gelatin capsules or cachets) or granules can be used. In these compositions, the active ingredient according to the invention is mixed with one or more inert diluents, such as starch, cellulose, saccharose, lactose or silica. These compositions can also comprise other substances, for example one or more lubricants such as magnesium stearate or talc, a colouring agent, a coating (sugar coating) or a varnish.

As liquid compositions for oral administration, pharmaceutically acceptable solutions, suspensions, emulsions, syrups and elixirs can be used containing inert diluents such as water, ethanol, glycerol, vegetable oils or paraffin oil. These compositions can also comprise other substances, for example wetting products, sweeteners, thickeners, flavouring agents or stabilizers

.

The sterile compositions for parenteral administration can preferably be aqueous or non-aqueous solutions, suspensions or emulsions. As solvent or vehicle, water, propyleneglycol, a polyethylene glycol, vegetable oils, in particular olive oil, suitable organic esters can be used. These compositions can also contain adjuvants, in particular wetting agents, isotoning agents, emulsifiers, dispersants and stabilizers. The sterilization can be done in different ways, for example by aseptic filtration, by incorporating in the composition of the sterilizing agents, by irradiation or by heating. They can be also be prepared in the form of sterile solid compositions, which can be dissolved at the time of use in an injectable sterile medium.

The compositions for rectal administration are suppositories or rectal capsules, which contain, in addition to the active ingredient, excipients such as cocoa butter, semi-synthetic glycerides or polyethylene glycols.

The sterile compositions for topical administration can be for example creams, ointments, lotions, collyria, collutories, nasal drops or aerosols.

The preferred administration methods are the parenteral route and the oral route.

The pharmacological doses depend on the sought effect and duration of the treatment; they are generally comprised between 0.001 mg/kg/day and 100 mg/kg/day, and preferably between 1 and 20 mg/kg/day.

These quantities can be administered in one or more doses.

An advantageous pharmaceutical composition according to the invention is a pharmaceutical composition characterized in that it comprises the compound as defined above, named OL-9, in combination with a pharmaceutically acceptable vector.

According to another embodiment, the invention also relates to a pharmaceutical composition characterized in that it comprises, as pharmaceutical vector, at least one of the compounds according to the invention in combination with a pharmaceutically active substance.

The invention also relates to the use of a compound according to the invention as a pharmaceutical vector.

By "pharmaceutical vector" is designated a compound according to the invention encouraging the passage of the substances with which it is found in combination, through biological membranes or teguments in particular the cytoplasmic membrane, the nuclear envelope or the skin.

Certain oligomers of the invention have the ability to interact with the membranes and penetrate into mammal cells in vitro and in vivo. This property can make them useful compounds for facilitating the penetration of molecules of therapeutic interest, such as the peptides or the oligonucleotides, through tissues in particular the skin, cell membranes or also through the nucleus of these cells. This property is useful for making it possible to increase the bio-availability of the peptides of interest. The peptide can be combined with its transporter in a covalent manner or be simply mixed with the latter. In the case of a covalent bond, a potentially hydrolyzable chemical bond, in particular an ester, oxime or amide bond or a chemical bond being able to be reduced, in particular a disulphide bridge is preferred. The ability of the transporter to ensure its function is linked to the presence of a certain number of basic residues, preferably an amine, guanidino or benzamide group. An advantageous number of residues ensuring the function of the transporter is n=4-10. The number of basic residues is advantageously comprised between 40% and 100%.

In fact, it is known from the prior art that peptides having a minimal number of consecutive arginine residues (oligo-Arg) can be internalized in the cells and serve to transport peptides or active ingredients to the chosen molecules (P. A. Wender et al., *Proc Natl Acad Sci U S A* 2000 Nov. 21;97(24):13003-8). It has been shown that the transporting ability of a molecule can depend on the relative position of arginines in the peptide sequence (J. Rothbard et al. *J Med Chem* 2002 Aug. 15;45(17):3612-8). In the case of a helicoidal structure, it has been shown that the positioning of the arginines on the same face of the helix thus leading to an amphipatic helix can improve the transport properties (A. Ho et al. *Cancer Res* 2001 Jan. 15;61(2):474-7). The design of the advantageous compounds of the invention can be rationalized thanks to the knowledge of the helicoidal structure described in the invention and the projection of which in a perpendicular plane at the axis of the helix can be used in order to visualize the amphipatic character of the compounds. An example of an amphipatic helix design based on the helicoidal structure 2.5 described in the invention is proposed below. The $A^2$ and $A^3$ groups are defined as previously, $A^2$ preferentially containing a guanidine, benzamidine or amide group and Pi indicating the position of the residue in the sequence:

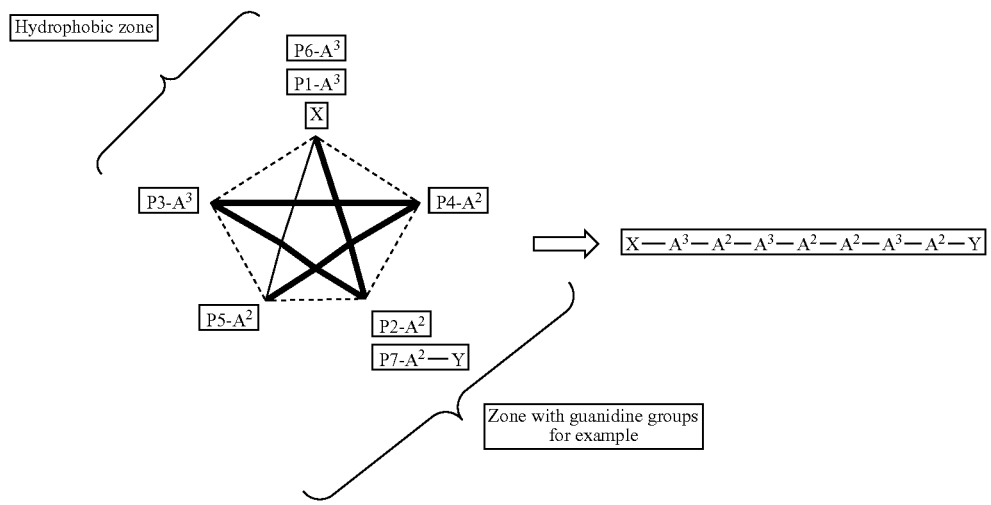

The following sequences defined previously can be used for the cell internalization:

Hexamers $$X\text{-}A^3\text{-}A^2\text{-}A^3\text{-}A^2\text{-}A^2\text{-}A^3\text{-}Y \quad (13)$$

$$X\text{-}A^2\text{-}A^3\text{-}A^2\text{-}A^2\text{-}A^3\text{-}A^2\text{-}Y \quad (14)$$

Heptamers $$X\text{-}A^3\text{-}A^2\text{-}A^3\text{-}A^3\text{-}A^2\text{-}A^3\text{-}A^2\text{-}Y \quad (15)$$

$$X\text{-}A^3\text{-}A^2\text{-}A^3\text{-}A^2\text{-}A^2\text{-}A^3\text{-}A^2\text{-}Y \quad (16)$$

$$X\text{-}A^2\text{-}A^3\text{-}A^2\text{-}A^2\text{-}A^3\text{-}A^2\text{-}A^3\text{-}Y \quad (17)$$

$$X\text{-}A^2\text{-}A^3\text{-}A^2\text{-}A^3\text{-}A^3\text{-}A^2\text{-}A^3\text{-}Y \quad (18)$$

Octamer $$X\text{-}A^3\text{-}A^2\text{-}A^3\text{-}A^2\text{-}A^2\text{-}A^3\text{-}A^2\text{-}A^3\text{-}Y \quad (19)$$

$$X\text{-}A^2\text{-}A^3\text{-}A^2\text{-}A^3\text{-}A^3\text{-}A^2\text{-}A^3\text{-}A^2\text{-}Y \quad (20)$$

Nonamer $$X\text{-}A^3\text{-}A^2\text{-}A^3\text{-}A^2\text{-}A^2\text{-}A^3\text{-}A^2\text{-}A^3\text{-}A^3\text{-}Y \quad (12)$$

The choice of the X group is important and advantageously comprises:

1) a functionality allowing subsequent ligation (binding) to the molecule (active ingredient, peptide, oligonucleotide) which is to penetrate into the cells.

or 2) the X group can also be the reaction product of the FITC (fluorescein isothiocyanate, commercial product Ref. 46950 from Fluka) with the amine of the following residue. This derivative is useful for proving that the studied oligomer does have cell internalization properties.

4 examples are represented below:

Choice 1) thiol group allowing anchoring to another molecule itself comprising a thiol or nucleimide group:

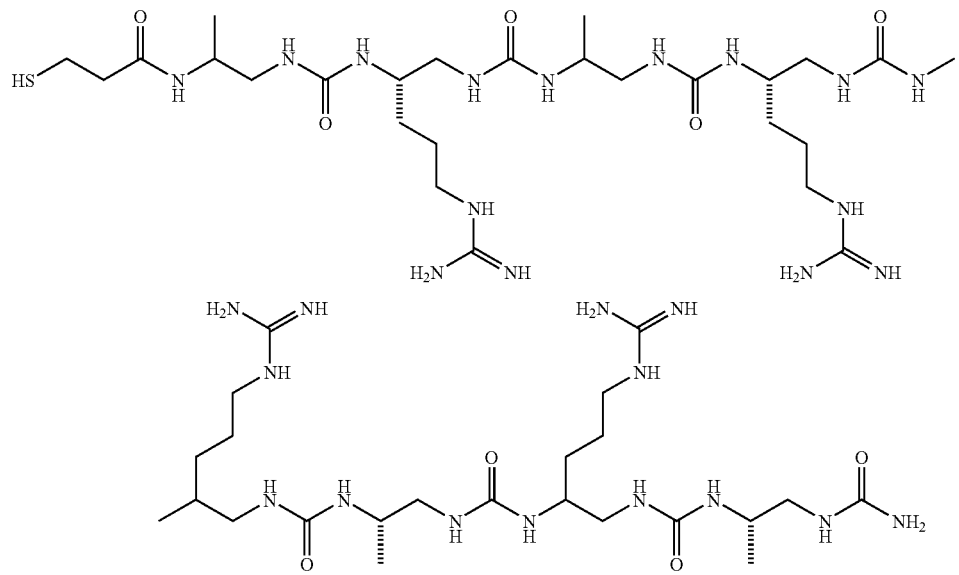

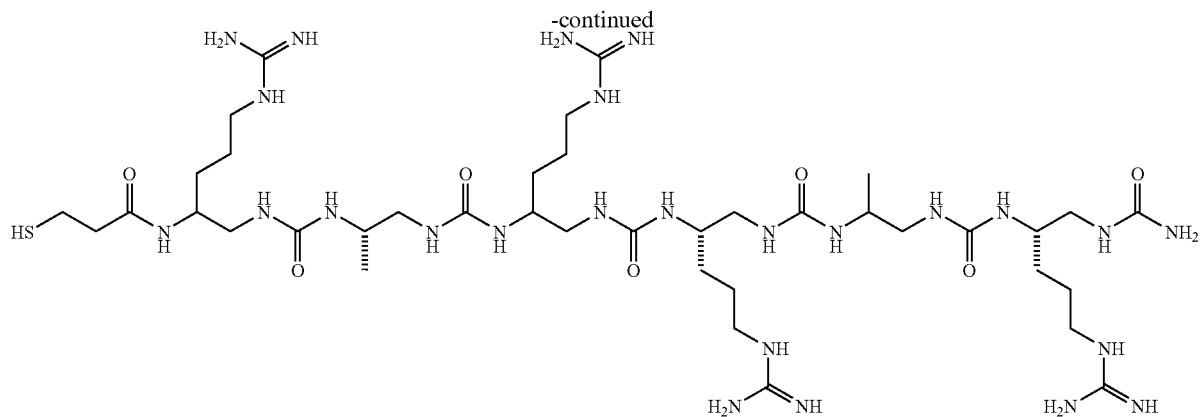
Choice 2) fluorescein function for a cell internalization test:
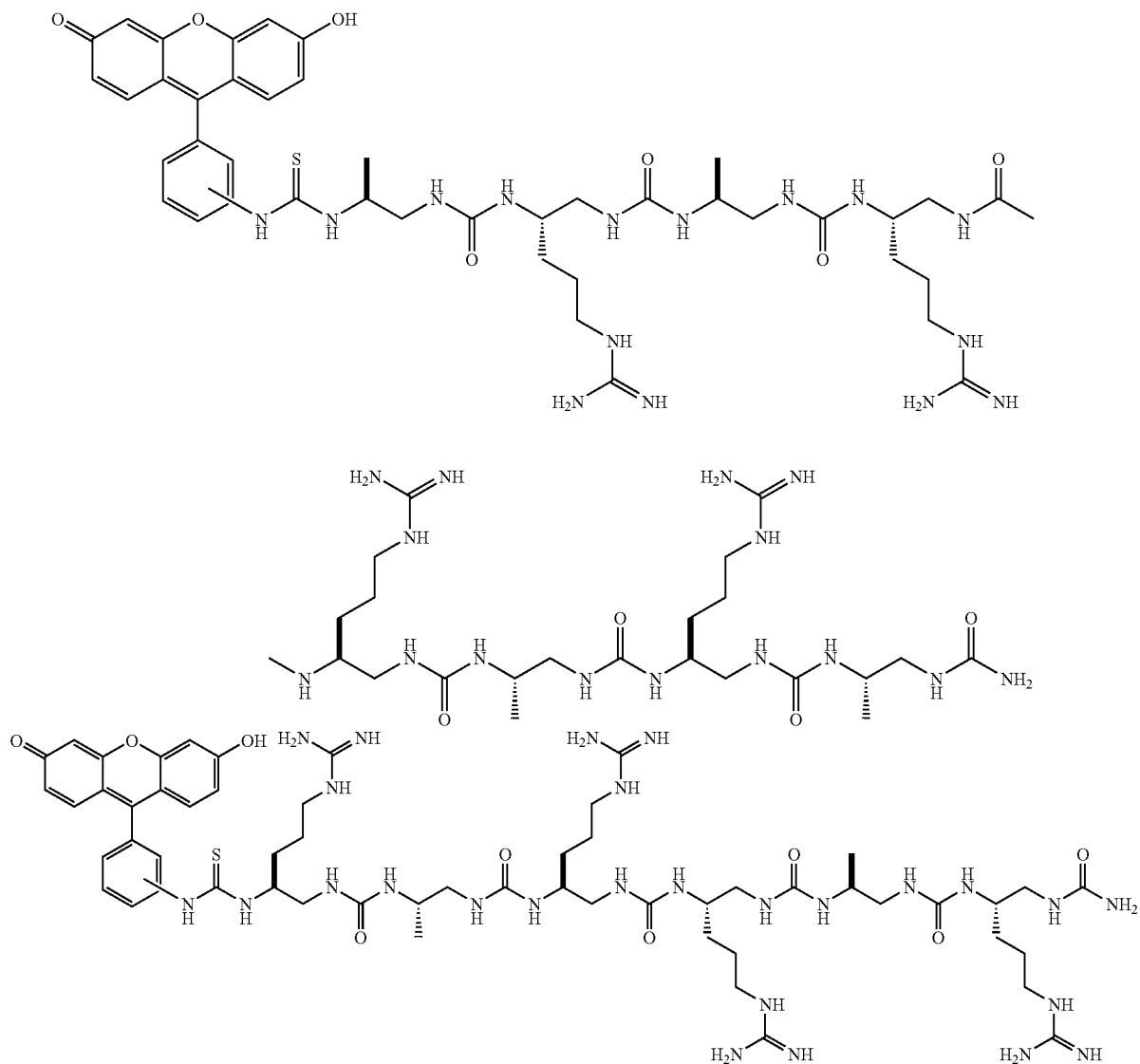

Figure 1:
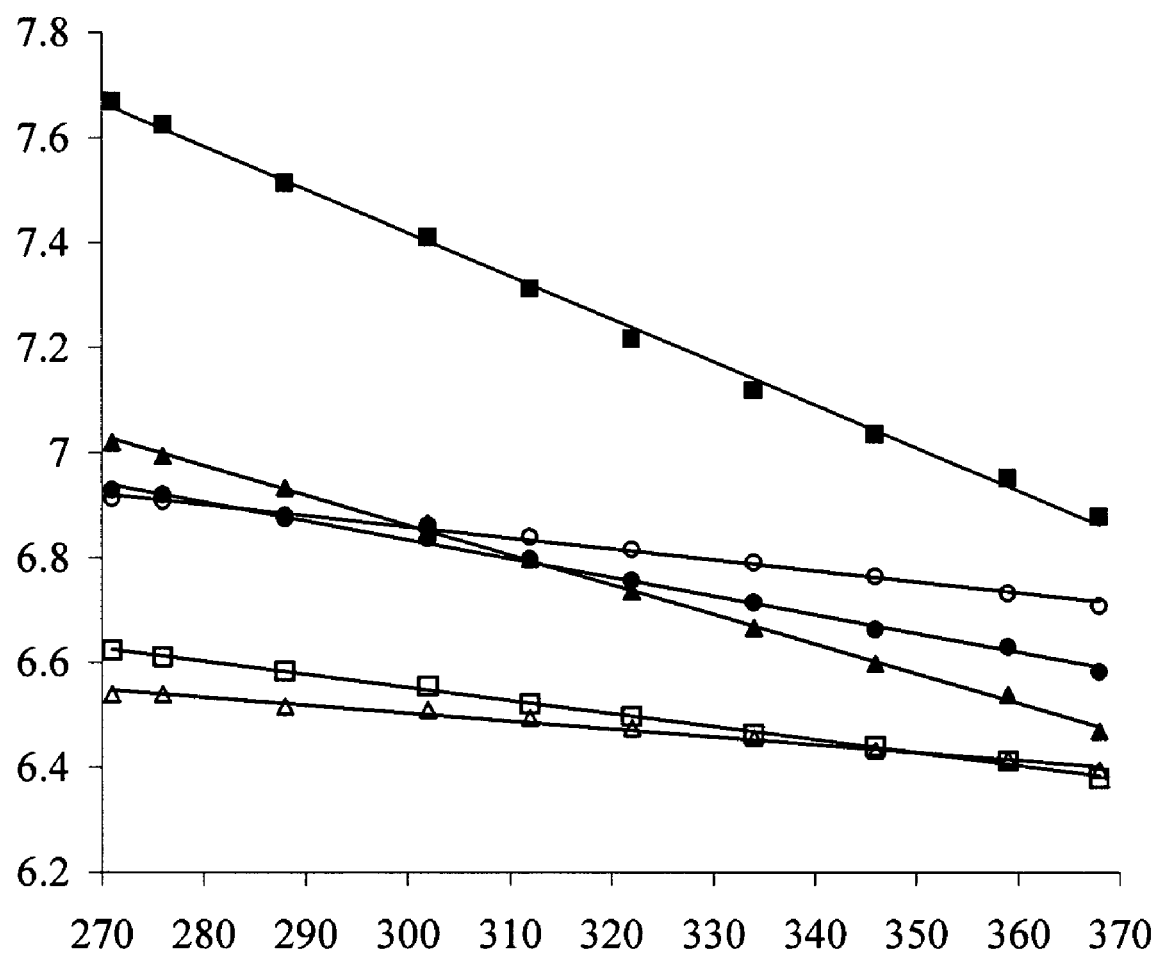
FIG. 1 represents the variation in the chemical shifts of the NH protons of the oligomer OL-7 as a function of temperature (in K).

The formula of a residue for the oligomers according to the invention should be recalled:

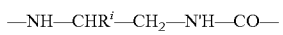

—NH—CHR$^i$—CH$_2$—N'H—CO—

The curve with the black squares corresponds to the proton of residue 2 (Ala); the curve with the black triangles corresponds to the proton of residue 3 (Val); the curve with the black circles corresponds to the proton of residue 4 (Tyr); the curve with the white squares corresponds to the proton of residue 5 (Ala); the curve with the white triangles corresponds to the proton of residue 6 (Val); the curve with the white circles corresponds to the proton of residue 7 (Tyr).

Figure 2:
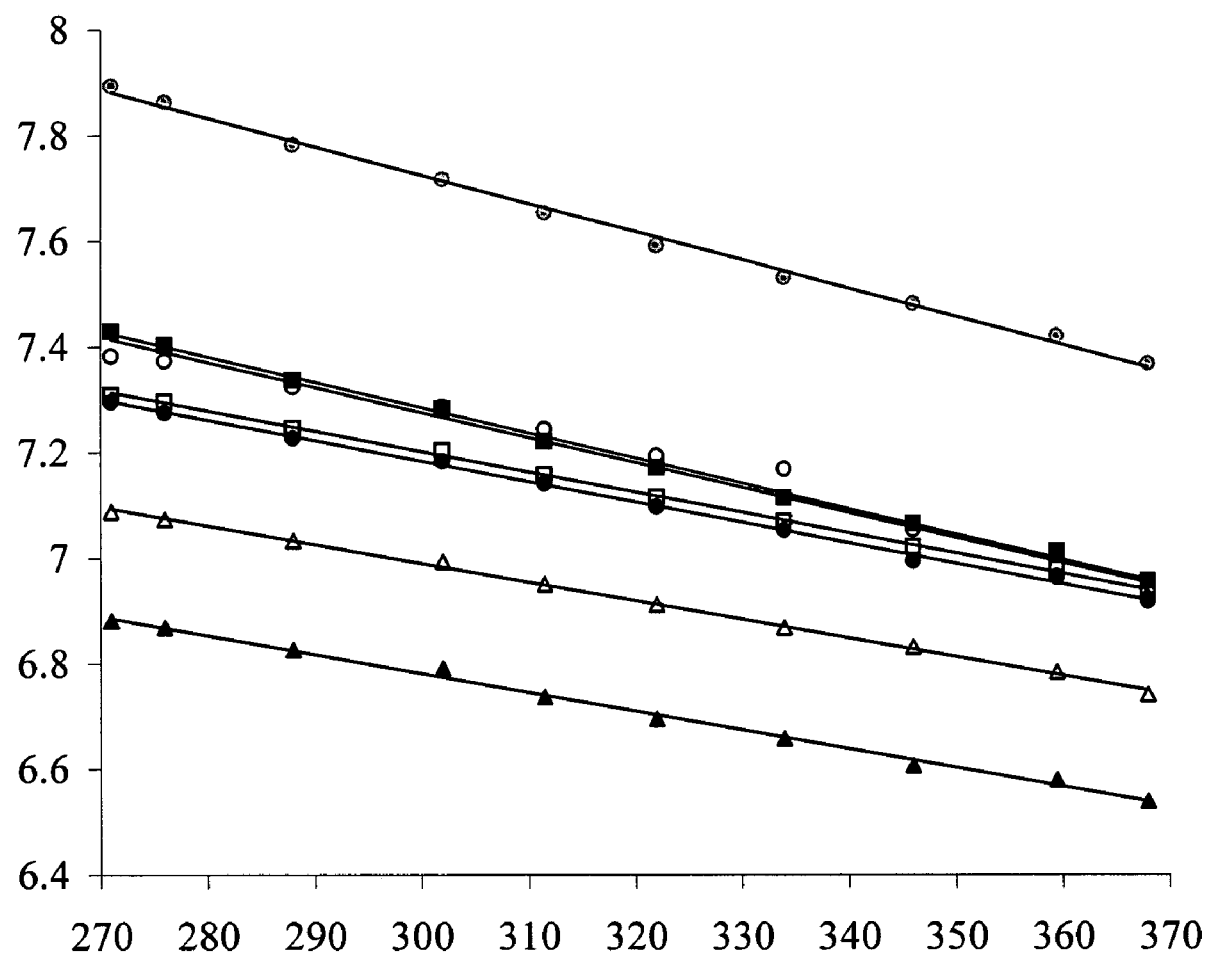

FIG. 2 represents the variation in the chemical shifts of the N'H protons of the oligomer OL-7 as a function of temperature (in K). The curve with the grey circles corresponds to the proton of residue 1 (Tyr); the curve with the black squares corresponds to the proton of residue 2 (Ala); the curve with the black triangles corresponds to the proton of residue 3 (Val); the curve with the black circles corresponds to the proton of residue 4 (Tyr); the curve with the white squares corresponds to the proton of residue 5 (Ala); the curve with the white triangles corresponds to the proton of residue 6 (Val); the curve with the white circles corresponds to the proton of residue 7 (Tyr).

For each of the curves in FIGS. 1 and 2, a linear regression has been carried out. These linear regressions make it possible to obtain the gradient of the straight lines and correspond to the temperature coefficients (see Tables 1 and 2). These values provide information on the accessibility of the proton vis-à-vis the solvent and its engagement in hydrogen bonds. The lower the absolute value of this figure (in particular below 4), the more accessible the proton is to the solvent and the more it is capable of being engaged in a hydrogen bond. These measurements therefore make it possible to verify that the central protons of the oligomer are more engaged in a hydrogen bond than the terminal protons.

Figure 3:
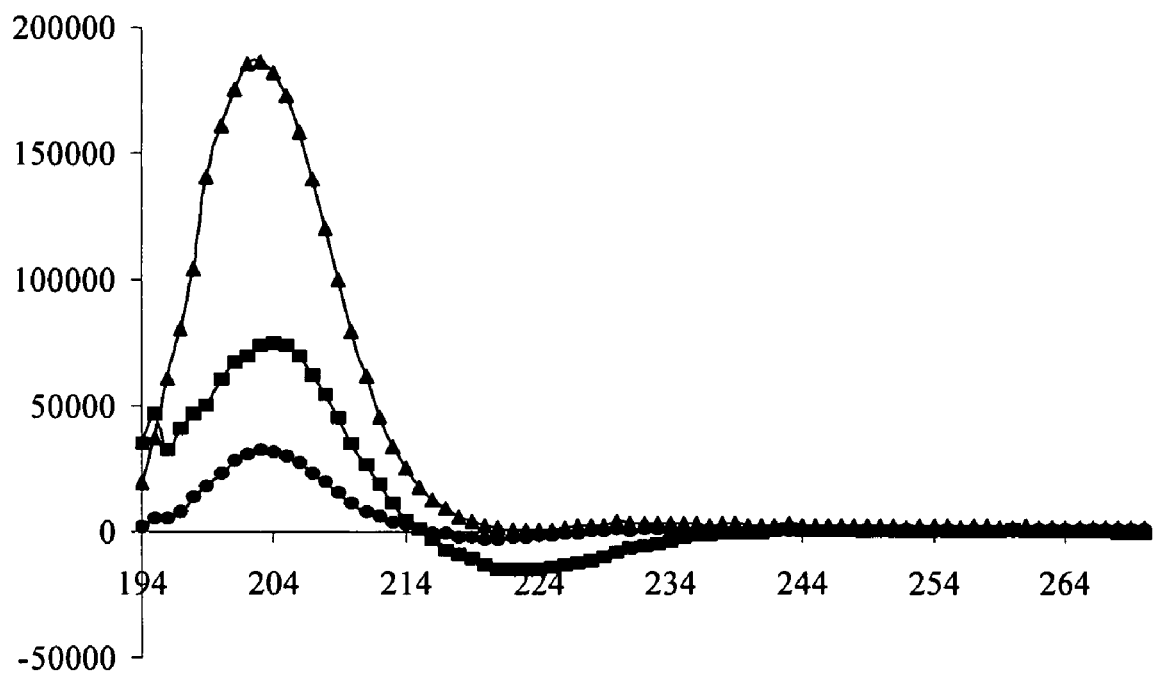

FIG. 3 represents the study by circular dichroism of compound OL-7 in different solvents, namely in methanol, water and trifluoroethanol. The curves of this figure represent θ as a function of the wavelength in nm.

θ is the molar ellipticity and is expressed in °.cm$^2$.dmol$^{-1}$.

θ can be positive or negative and its value is linked to the secondary structure of the oligomers. This phenomenon (Cotton effect) is extremely well-known for the peptides and for other types of non-natural oligomers.

The curve with the black triangles corresponds to compound OL-7 studied in methanol; the curve with the black circles corresponds to compound OL-7 studied in trifluoroethanol and the curve with the black squares corresponds to compound OL-7 studied in water.

Figure 4:
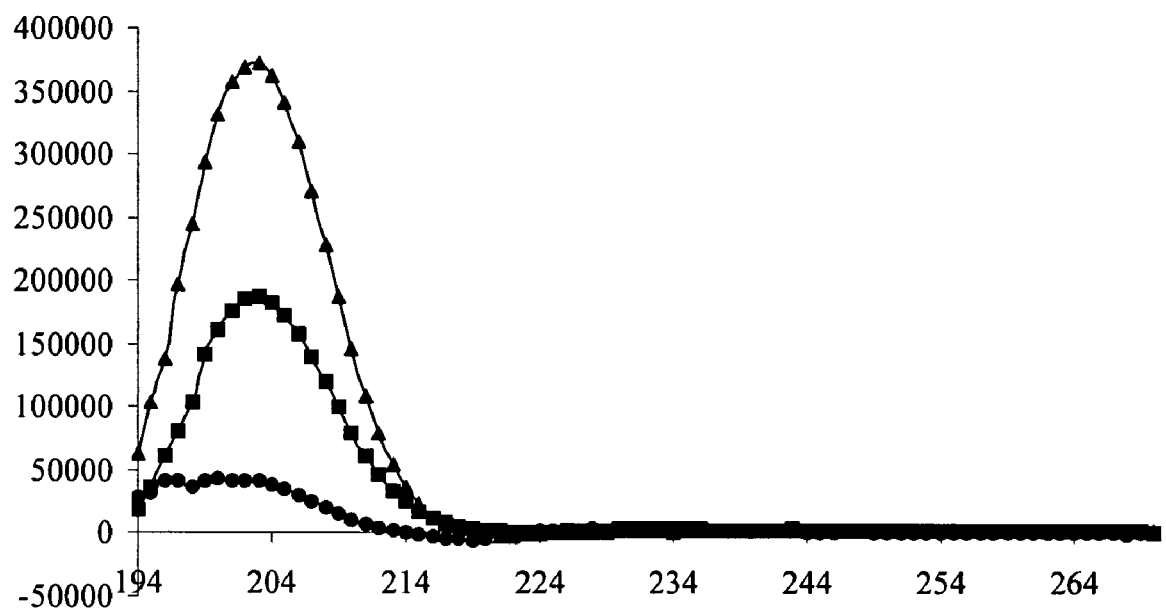

FIG. 4 represents the study by circular dichroism of compounds OL-6 (hexamer), OL-7 and OL-9 in methanol.

Compound OL-6 corresponds to the following formula:

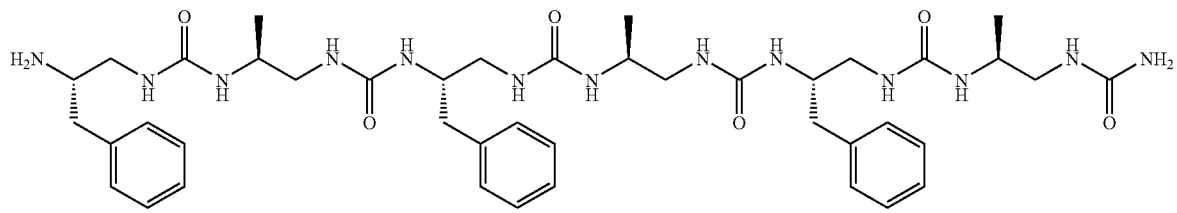

The curves of this figure represent θ (molar ellipticity in °.cm$^2$.dmol$^{-1}$) as a function of the wavelength in nm.

The curve with the black circles corresponds to compound OL-6; the curve with the black squares corresponds to compound OL-7 and the curve with the black triangles corresponds to compound OL-9.

Figure 5:
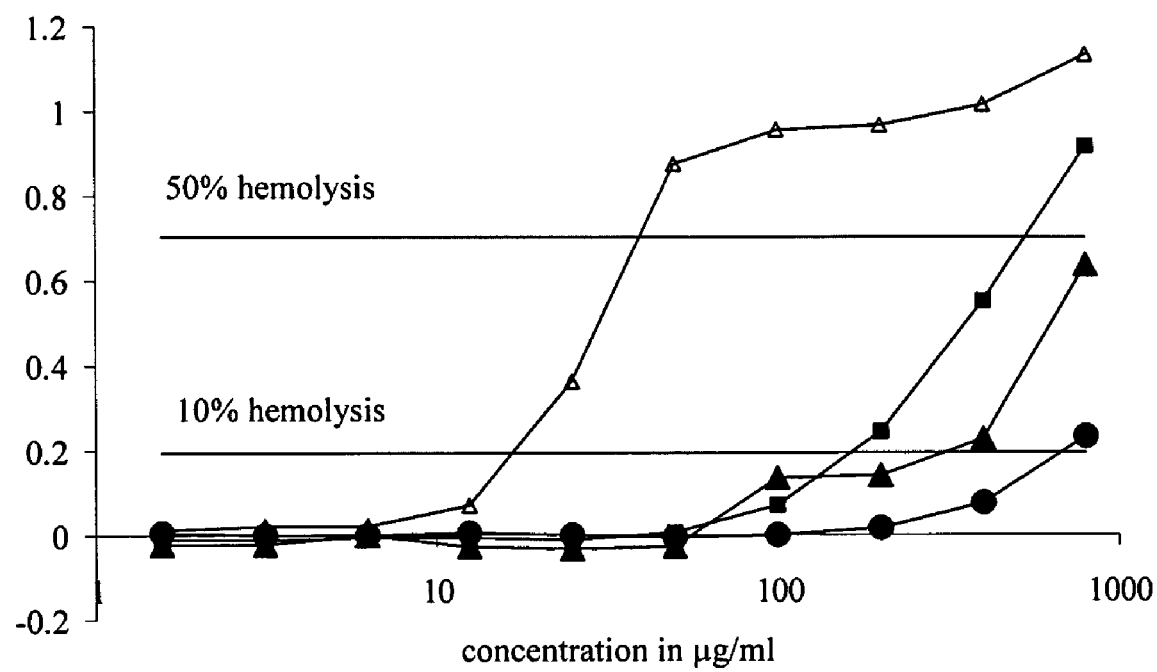

FIG. 5 represents the results of the hemolysis tests carried out on compound OL-9 according to the invention.

This graph represents the optical density as a function of the concentration in μg/ml of the compound tested.

The curve with the white triangles corresponds to cetylpyridinium chloride (this compound serves as an internal control); the curve with the black squares corresponds to the control D peptide; the curve with the black triangles corresponds to the control L peptide and the curve with the black circles to compound OL-9.

The control D peptide is represented by the following sequence:

H-DTyr-DLys-DLeu-DVal-DPhe-DLys-DAla-DVal-DTyr-NH$_2$

The control L peptide is represents by the following sequence:

H-Tyr-Leu-Val-Phe-Lys-Ala-Val-Tyr-NH$_2$

EXAMPLES

Preparation of the Compounds of the Invention in Particular OL-9 AND OL-7

The oligomers of the invention and in particular OL-9 and OL-7 were synthesized in solid phase from a commercial Rink amide resin (4-(2',4'-Dimethoxyphenyl-Fmoc-aminomethyl)phenoxyacetamido-4-methylbenzhydrylamine resin) on a scale of 50 μmol from the succinimidyl carbamates 1 carrying the side chains of Ala, Val, Leu, Phe, Tyr(tBu), Lys(Boc), Arg(PMC) or Arg(Pbf); (prepared according to Guichard et al., *Tetrahedron Lett.*, 2000, 41, 1553-1557).

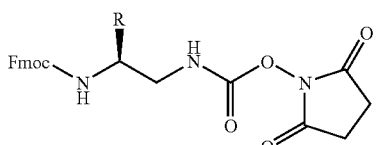

| 1 | R |
|---|---|
| a | Me |
| b | iPr |
| c | iBu |
| d | Bn |
| e | Bn(OtBu) |
| f | (CH$_2$)$_4$NHBoc |

The desired carbamate 1 (4 equivalents) in 2 ml of DMF is added to a suspension of the abovementioned resin in DMF (2 ml) followed by N-methylmorpholine (1 equivalent). The reaction is left to take place for 90 minutes and is recommenced, after filtration of the resin. The Fmoc group is then cleaved by treatment with 20% piperidine in DMF. The technique of washing and filtration of the resin as well as deprotection of the Fmoc group are those commonly used in peptide synthesis in solid phase. The whole of the operation (coupling and deprotection of the Fmoc) is recommended several times with the carbamates 1 possessing the side chains of the following residues in the sequence in order to produce after cleavage of the resin (TFA, water/triisopropylsilane: standard cleavage used in peptide synthesis in solid phase in Fmoc strategy) the crude products OL-7 and OL-9, with a purity of 65% and 32% respectively (determined by HPLC). The pure product is characterized by mass spectrometry (MALDI-MS) and by HPLC.

RESULTS

OL-7:
HPLC retention time: 14.58 min (A: 0.1% TFA in H$_2$O; B: 0.08% TFA in CH$_3$CN, 5-65% B over 20 minutes) (TFA=trifluoroacetic acid).
MS (MALDI-TOF): 1051.5 [M+H]$^+$ OL-9:
HPLC retention time: 15.2 min (A: 0.1% TFA in H$_2$O; B: 0.08% TFA in CH$_3$CN, 5-65% B over 20 minutes) (TFA=trifluoroacetic acid).
MS (MALDI-TOF): 1393.1 [M+H]$^+$ The conformational study of the two oligomers OL-7 and OL-9, synthesized in solid phase, was carried out by mono and two-dimensional Magnetic Nuclear Resonance (NMR) initially in pyridine-d5 (in pyridine, the signals of the NH protons are better dispersed than in chloroform or methanol, and the attribution of the signals thereof is facilitated) then in deuterated methanol CD$_3$OH.

The attribution of the resonances as well as the determination of the sequence was carried out by DQF-COSY, TOCSY and ROESY experiments.

It is recalled by definition that DQF-COSY (Double Quantum filtered correlated spectroscopy), TOCSY (Total Correlated Spectroscopy) and ROESY (Rotating frame overhauser effect spectroscopy) are standard spectroscopy techniques.

A certain amount of significant data for the determination of the secondary structure was extracted from the monodimensional spectra and the COSY experiments.

Tables 1 and 2 hereafter indicate the temperature coefficients (in ppb.K$^{-1}$) calculated for the protons of the NH and N'H groups of residues 1 to 7 of compound OL-7 (See FIGS. 1 and 2), and of residues 1 to 9 of compound OL-9.

TABLE 1

| residue | N'H | NH |
|---|---|---|
| 1 | −5.3 | |
| 2 | −4.8 | −8.2 |
| 3 | −3.6 | −5.6 |
| 4 | −3.8 | −3.6 |
| 5 | −3.8 | −2.5 |
| 6 | −3.5 | −1.5 |
| 7 | −4.7 | −2.1 |

TABLE 2

| residue | N'H | NH |
|---|---|---|
| 1 | −7.8 | |
| 2 | −6.7 | −8.7 |
| 3 | −3.25 | −5.2 |
| 4 | −5 | −2.4 |
| 5 | −5 | −0.8 |
| 6 | −4.2 | −1.2 |
| 7 | −4.75 | −1.88 |
| 8 | −3.75 | −1.1 |
| 9 | −5 | −2.5 |

These figures are established from the chemical shift curves as a function of temperature by calculating the gradients of the straight lines obtained by linear regression.

These temperature coefficients are expressed in ppb.K$^{-1}$ and are denoted $\delta\Delta/\delta T$.

Measurement of the temperature coefficients (heating to approximately 100° C. for OL-7) on these two molecules suggests that the NH protons of residues 4-7 for OL-7 and 4-9 for OL-9 are not very accessible with the solvent and are potentially linked by a hydrogen bond ($-\Delta\delta/\Delta T<2.5$ for the nonamer) (with the exception in general of the two N-terminal residues for which the temperature coefficients are above 5). The N'H protons of the central residues have more negative temperature coefficients ($3.5<-\Delta\delta/\Delta T<3.8$ for residues 3-7 in the case of the oligomer OL-7); they are therefore probably more accessible to the solvent and therefore less engaged in hydrogen bonds than each of the corresponding NHs within each urea function.

Furthermore, the coupling constants J(NH, $^\beta$OCH) are high (with the exception of the two N-terminal residues, the constants are of the order of 9-10 Hz) and are not very sensitive to temperature changes (see Tables 3 and 4 hereafter).

TABLE 3

Study of the variation in the coupling constants $^3$J(NH, $^\beta$CH) in Hz for residues 2 to 7 of OL-7 as a function of temperature

| temperature (K) | residues | | | | | |
| | 2 | 3 | 4 | 5 | 6 | 7 |
|---|---|---|---|---|---|---|
| 368 | — | 10.1 | 10.3 | 10.1 | 10.3 | 8.5 |
| 360 | — | 10.3 | 10.3 | 10.3 | 10.5 | 8.9 |
| 346 | — | 10.1 | 10.3 | 10.3 | 10.3 | 9.1 |
| 332 | 9.9 | 10.3 | 10.3 | 10.5 | 10.3 | 9.3 |
| 322 | — | 10.7 | 10.5 | 10.5 | 10.5 | 9.3 |
| 312 | — | 10.5 | 10.5 | 10.5 | 10.7 | — |
| 302 | 9.3 | 10.3 | 10.7 | 10.5 | 10.7 | 8.7 |
| 288 | 9.3 | 10.3 | 10.7 | 10.5 | 10.7 | 8.7 |

TABLE 4

Study of the variation in the coupling
constants $^3J(N'H, {}^\beta CH)$ in Hz for
residues 2 to 9 of OL-9 as a function of temperature

| | residues | | | | | | | |
|---|---|---|---|---|---|---|---|---|
| temperature (K) | 2 | 3 | 4 | 5 | 6 | 7 | 8 | 9 |
| 308 | 9.5 | 10.1 | 11.3 | 10.4 | 10.1 | 10.1 | 10.7 | 7.9 |
| 332 | — | 9.8 | 10.4 | 9.8 | 10.4 | 10.4 | 10.1 | 8.9 |

Moreover, the two geminal protons on the $^\alpha C$ have significant differences in chemical shift ($1.3<\Delta\delta<1.6$ ppm for the central residues 3-6 and $\Delta\delta=1.0$-1.1 ppm for residues 2 and 7). This difference which reflects a well-defined and distinct spatial arrangement for each of the two diastereotopic protons carried by the $^\alpha C$ remains constant throughout the temperature range.

In the case of the oligomer OL-7, a careful examination of the values of the constants $^3J(^\alpha CH_2,N'H)$ and $^3J(^\beta CH,^\alpha CH_2)$ for residue 3 at 332K (see Table 5 hereafter), reveals that the $^\alpha CH$ proton which is least unimmune from interference possesses a high coupling constant with N'H (10 Hz) and a low coupling constant with $^\beta CH$ (2.5 Hz), which implies that this proton is in a practically antiperiplanar arrangement relative to N'H and synclinal relative to $^\beta CH$.

TABLE 5

Chemical shifts and coupling constants for the protons
of residue 3 of compound OL-7.

| Proton | δ (ppm) | J (Hz) |
|---|---|---|
| NH | 6.64 | $^3J(NH,{}^\beta CH) = 10$ |
| $^\beta CH$ | 4.02 | $^3J(^\beta CH,^\alpha CH^{Si}) = 2.5$; $^3J(^\beta CH,^\alpha CH^{Re}) = 11$ |
| $^\alpha CH^{Re}$ | 2.53 | $^2J(^\alpha CH^{Re},^\alpha CH^{Si}) = 14$ |
| $^\alpha CH^{Si}$ | 3.96 | |
| N'H | 6.66 | $^3J(N'H,^\alpha CH^{Si}) = 10$; $^3J(N'H,^\alpha CH^{Re}) = 3.5$ |

Subsequently, the stereospecific attribution was carried out on the assumption that the $^\alpha CH$ protons with a large coupling constant $^3J(^\alpha CH_2,N'H)$ in the COSY spectrum are the $^\alpha CH_{Si}$ protons. These data indicate that the oligomers OL-7 and OL-9 adopt a stable secondary structure, well-defined in solution.

In order to obtain more precise information on the secondary structure, ROESY spectra were recorded with a mixing time of 300 ms. A large number of NOE inter-residue correlations i/(i+2) can be observed in pyridine for OL-7 and OL-9 but also in methanol with, in particular, intense $^\beta CH_i/N'H_{i+2}$, $^\beta CH_i/N'H_{i+2}$ correlations repeated throughout the sequence (see Table 6 hereafter).

It is recalled that the NOE correlations correspond to the measurement of the "overhauser" effect between two protons (K. Wüthrich, NMR of proteins and nucleic acids, 1986, J. Wiley & Sons, Inc).

TABLE 6

Interresidues NOEs for OL-7 in pyridine-$d_5$ at 332K

| H atom (residue i) | H atom (residue j) | NOE[a] | k = j − i |
|---|---|---|---|
| N'H (1) | NH (2) | s | 1 |
| $^\alpha H_{Si}$ (1) | NH (4) | w | 3 |
| $^\beta CH$ (1) | N'H (3) | m | 2 |

TABLE 6-continued

Interresidues NOEs for OL-7 in pyridine-$d_5$ at 332K

| H atom (residue i) | H atom (residue j) | NOE[a] | k = j − i |
|---|---|---|---|
| N'H (2) | NH (3) | s | 1 |
| $^\beta CH$ (2) | N'H (3) | m | 1 |
| $^\beta CH$ (2) | NH (4) | m | 2 |
| $^\beta CH$ (2) | N'H (4) | m | 2 |
| N'H (3) | NH (4) | s | 1 |
| $^\alpha H_{Si}$ (3) | N'H (5) | s | 2 |
| $^\beta CH$ (3) | NH (5) | s | 2 |
| $^\beta CH$ (3) | N'H (5) | s | 2 |
| $^\beta CH$ (3) | $^\alpha H_{Re}$ (5) | s | 2 |
| $^\gamma CH$ (3) | $^\alpha H_{Re}$ (5) | w | 2 |
| $^\delta CH$ (3) | $^\alpha H_{Re}$ (5) | s | 2 |
| N'H (4) | NH (5) | s | 1 |
| $^\beta CH$ (4) | NH (6) | m | 2 |
| $^\beta CH$ (4) | N'H (6) | s | 2 |
| N'H (5) | NH (6) | s | 1 |
| $^\alpha H_{Si}$ (5) | NH (7) | w | 2 |
| $^\alpha H_{Si}$ (5) | N'H (7) | m | 2 |
| $^\beta CH$ (5) | NH (7) | s | 2 |
| $^\beta CH$ (5) | N'H (7) | m | 2 |
| $^\beta CH$ (5) | $^\alpha H_{Re}$ (7) | m | 2 |
| $^\gamma CH$ (5) | $^\alpha H_{Re}$ (7) | m | 2 |
| N'H (6) | NH (7) | s | 1 |
| $^\beta CH$ (6) | N'H (7) | w | 1 |

[a]strong (s), <2.8 Å; medium (m), <3.8 Å; weak (w), <5.5 Å.

This repetition of the NOE correlations throughout the sequence is in keeping with a 2.5-(P) type helix already proposed in the case of γ-peptides. It should be recalled that a 2.5-(P) helix is a right-handed helix (P) comprising 2.5 residues per turn.

The NOEs identified in the spectrum recorded in pyridine were classified by category of distances as a function of the volume of the peaks. On the basis of these distance constraints and on information relating to certain torsion angles of the skeleton derived from the coupling constants $^3J$, a molecular modeling by simulated annealing and a study by molecular dynamics were carried out on the heptamer OL-7 in collaboration with the Didier Rognan group (UMR CNRS-ULP 7081, Strasbourg). This study confirmed the helical structuration of this oligomer and the stability of the structure obtained.

It is a right-handed helix possessing a pitch of approximately 5 angströms and a number of residues per turn of the helix of approximately 2.5. The helix is stabilized throughout the sequence by a network of intramolecular hydrogen bonds between the C=O of an i residue and the two NHs (N'H and NH) of the same urea function corresponding to the residues i+2 and i+3 respectively. The hydrogen bond $C=O_i$—$NH_{i+3}$ (which closes a pseudoring with 14 atoms) is statistically more present than the hydrogen bond $C=O_i$—$N'H_{i+2}$ (which closes a pseudoring with 12 atoms).

On the basis of the NMR study in methanol confirming the structure in this solvent, a circular dichroism (CD) study was carried out in methanol but also in water and in trifluoroethanol (see FIG. 3). This study revealed a signal characteristic of the helicoidal form (maximum at 205 nm) for the heptamer and for the nonamer in methanol and an absence of signal for shorter oligomers (see FIG. 4): a hexamer produces virtually no signal at this wavelength. It can therefore be concluded that a minimum of 7 urea bonds is necessary for the formation of the helix in methanol.

In the case of the oligomer OL-9, the study of the signal at 205 nm as a function of temperature indicates that this is not very sensitive to an increase in temperature and suggests that the secondary structure persists up to 60° C. and that the unfolding mechanism is non-cooperative (a straight line of negative gradient is obtained). In trifluoroethanol, the characteristic signal disappears since in water a part of the signal remains at 205 nm.

The presence of a strong signal at 205 nm characteristic of the secondary helical structure suggests that circular dichroism can be used advantageously in order to rapidly identify the presence of a secondary structure in urea oligomers of varied sequence.

HEMOLYSIS TEST

Principle of the Test:

A compound acting on the membranes of bacteria can potentially disturb the membranes of mammalian cells. The red blood cells or erythrocytes serves as a model of eukaryotic cells where the degree of membrane permeation is easily evaluated by measuring the quantity of hemoglobin released through the pores of the embrittled membranes and the concentration of which is directly proportional to the optical density at 450 nm.

Use of the Test:

The erythrocytes are prepared from freshly sampled monkey blood (macaque). The heparinized blood is centrifuged and washed three times with cold PBS and resuspended at 10% (v/v) in PBS. 10 µl of an aqueous solution of the products to be tested are added to 90 µl of suspension of red blood cells. The erythrocytes are incubated for one hour at 37° C. The suspension is centrifuged in order to recover the supernatant which is more or less red depending on the degree of hemolysis. The concentration of hemoglobin released in the supernatant is measured by the optical density at 450 nm. In the negative control the red blood cells are incubated in the absence of product and show an OD of 0. 100% hemolysis is obtained with 100 µg cetylpyridinium chloride per ml of suspension. The degree of hemolysis is evaluated with respect to the positive control for the different concentrations of the products tested.

Results:

The results of the hemolysis test are summarized in the graph in FIG. 5.

It is noted that for a concentration of 1 mg/ml, OL-9 leads to 10% of hemolysis whereas the control L and D peptides with the same side chains lead respectively, at the same concentration, to approximately 50% and to more than 60% hemolysis. It can therefore be concluded that the natural peptides are relatively toxic for the eukaryotic cells whereas the oligomer OL-9, which demonstrated an antimicrobial activity, is only slightly toxic, or not toxic for the eukaryotic cells at doses of the order of 1 mg/ml.

Evaluation Test of Antimicrobial and/or Antifungal Activity:

Principle of the Test:

The compounds tested all form part of the polyurea class and were obtained in the laboratory by chemical route. Tests for the inhibition of the growth of bacteria and fungi were carried out in liquid tests. The specific activity of each molecule is expressed by the minimal inhibitory concentration on the growth of the bacteria and/or fungi, called MIC. The MIC is a value specific to each compound and varies as a function of the organisms tested. It should be noted that the MIC values follow a logarithmic progression, which is due to a two-by-two dilution of the compounds tested in a series of tests. The molecules tested were presented in the form of salts which are soluble in water and thus the culture medium of the microorganisms.

Use of the Test:

For carrying out the tests, 96-well plates were used. Each well contains 90 µl of a suspension of bacteria diluted in PB medium (Poor Broth, Difco) in order to have a final concentration of 1 mOD. 10 µl of compound in solution in sterile water at concentrations ranging from 1 mg/ml to 2 µg/ml are added to the tests. The plates are placed under stirring at 29° C. for 24 hours. The growth of the bacteria is measured by measuring the turbidity of the culture medium and measuring the OD at 595 nm. The value of the MIC corresponds to the concentration of the substances to be tested where no growth of bacteria is noted (OD=0).

The antifungal tests are carried out in similar fashion with ½ PDB (Potato dextrose broth, Difco) as culture medium and 10,000 spores per ml of culture. An optical control under a reverse microscope is necessary in the case of the fungi in order to evaluate the formation of the mycelia of the filamentous fungi (*Aspergillus fumigatus, Neurospora crassa*). The CMC is determined after culture for 48 hours at 29° C. and corresponds to the concentration where no formation of mycelium is observed.

Internal controls were used. These involved cetylpyridinium chloride and dequalinium bromide, standard antiseptics (Merck index).

Results:

Oligomer 9 (OL-9)

M.W. (+3 TFA)=1732.82 g.mol$^{-1}$

L peptide (control)

10 M.W. (+3 TFA)=1472.44 g.mol$^{-1}$

| | Minimum inhibitory concentration | |
|---|---|---|
| Bacteria | OL-9 | Peptide L (control) |
| *E. coli* D363 | 4.1 µg/ml | 3.8 µg/ml |
| | 2.4 µM | 2.6 µM |
| *Staphylococcus aureus* | 8.1 µg/ml | >121 µg/ml |
| | 4.7 µM | |
| *Salmonella cloacae* | 4.1 µg/ml | 3.8 µg/ml |
| | 2.4 µM | 2.6 µM |
| *Micrococcus luteus* | 4.1 µg/ml | 3.8 µg/ml |
| | 2.4 µM | 2.6 µM |
| *Pseudomonas aeruginosa* | 32.5 µg/ml | 121 µg/ml |
| | 19 µM | 82 µM |
| *Aspergillus fumigatus* | >100 µg/ml | 121 µg/ml |
| | | 82 µM |
| *Neurospora crassa* | 32.5 µg/ml | 30 µg/ml |
| | 18 µM | 20 µM |

The concentrations of the compounds tested in a series of tests vary from 100 µg/ml of culture to 0.2 µg/ml. Activities comprised between values of 10 to 50 µg/ml 15 are considered as low. Compounds with activities between 0.1 and 10 µg have activities of the same order of magnitude as commercial antibiotics. The best of the compounds tested have an activity of 3 µg/ml with a wide spectrum of activities.

It emerges from this study that the oligomer OL-9 has a wide spectrum of antibacterial activity (*E Coli, Staphylococcus aureus, Salmonella cloacae, Pseudomonas aeruginosa*) and that this family of non-natural oligomers and their oxygenated analogues (oligocarbamates) represent candidates of interest for the development of novel antibiotics.

Evaluation Test of the Internalization Ability of the Oligomers

The oligoureas are dissolved in phosphate buffer (PBS, pH=7.2), their concentration is determined by absorption of the fluorescein at 490 nm. The weighing of the sample followed by its dissolution in a known volume of PBS buffer makes it possible to establish with precision the concentration of the transporter. The concentrations determined by UV spectroscopy are consistent with the quantities measured manually. The T Jurkat cell line, cultured in 10 µl of fetal calf serum in Dulbecco's Modified Eagle medium (DMEM) was used for all the cell internalization measurements. Variable quantities of oligomers are added at $3 \times 10^5$ cells in a total volume of 200 µl in wells of microtitration plates and are incubated for 3 minutes at 23° C. The plates are centrifuged, the cells are isolated and washed 3 times with cold PBS then resuspended in PBS containing 0.1% of propidium iodide. The cells are then analyzed by fluorescence flow cytometry (Faxscan, Becton Dickinson) and the cells stained with propidium iodide excluded from the analysis.

The invention claimed is:
1. A compound of formula:

$$X-(A)_n-Y, \quad (I)$$

in which:
n varies from 6 to 20,
X represents hydrogen, $R_aCO$, $R_aOCO$, $R_aNHCO$, $R_aSO_2$ or $R_aNHCS$,
  $R_a$ is fluorescein, (C1-C10 alkyl), (C1-C10) alkenyl, (C1-C10) alkynyl, (C5-C12) aryl, (C5-C14) aralkyl, or (C1-C5) heteroaryl, which groups are unsubstituted or substituted by 1 to 6 substituents chosen from: halogen, $NO_2$, OH, (C1-C4) alkyl, $NH_2$, CN, trihalomethyl, (C1-C4) acyloxy, (C1-4) dialkylamino, guanidino, SH, and maleimide, provided that X is not H when n is 6,
A represents either:

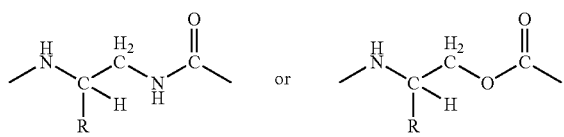

R being hydrogen, an amino acid side chain, (C1-C10) alkyl, (C1-C10) alkenyl, (C1-C10) alkynyl, (C5-C12) aryl, (C5-C14) aralkyl or (C1-C10) heteroaryl, said groups being unsubstituted or substituted by 1 to 6 substituents chosen from: halogen, $NO_2$, OH, amidine, benzamidine, imidazole, alkoxy, (C1-C4) alkyl, $NH_2$, CN, trihalomethyl, acyloxy (C1-C4), dialkylamino (C1-C4), and guanidino, and with the proviso that approximately 10% to approximately 50% of the R substituents are amino acid side chains of basic character,
Y is an $NR_bR_c$ group, $R_b$ and $R_c$ having the same meaning as for R,
provided that the compounds of the following formulae are excluded:

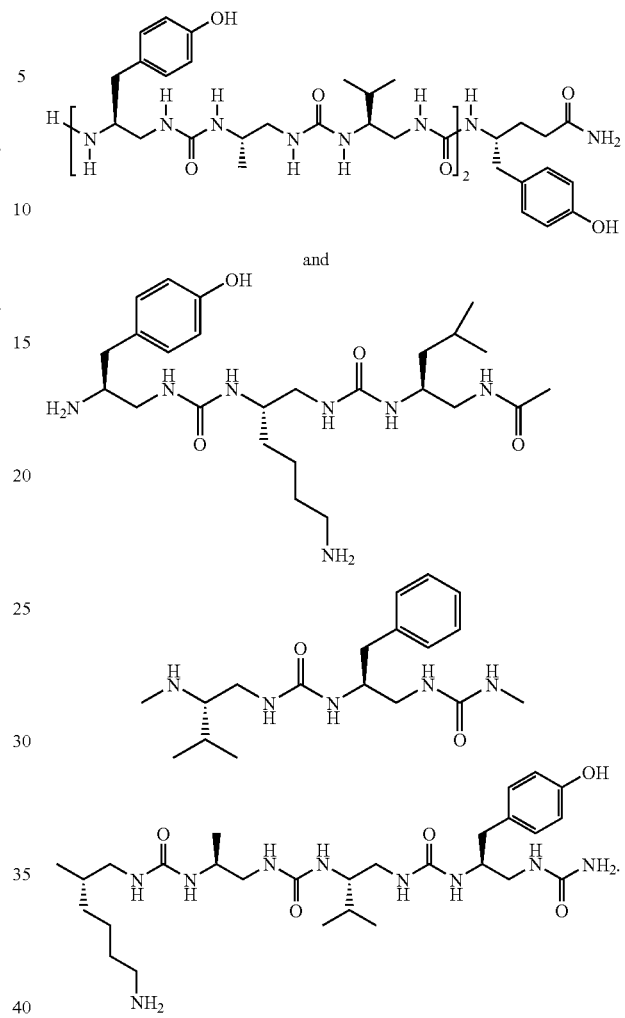

2. The compound according to claim 1, wherein n is equal to 6, 7, 8 or 9, and wherein said compound has one of the following formulae:

| | |
|---|---|
| $X-A^3-A^2-A^3-A^2-A^2-A^3-Y$ | (13) |
| $X-A^3-A^2-A^3-A^3-A^2-A^3-A^2-Y$ | (15) |
| $X-A^2-A^3-A^2-A^3-A^3-A^2-A^3-Y$ | (18) |
| $X-A^3-A^2-A^3-A^2-A^2-A^3-A^2-A^3-Y$ | (19) |
| $X-A^2-A^3-A^2-A^3-A^3-A^2-A^3-A^2-Y$ | (20) |
| $X-A^1-A^2-A^3-A^3-A^1-A^2-A^3-A^1-A^3-Y$ | (1) |
| $X-A^1-A^2-A^3-A^3-A^1-A^2-A^3-A^3-A^1-Y$ | (2) |
| $X-A^1-A^2-A^3-A^3-A^1-A^3-A^2-A^1-A^3-Y$ | (3) |
| $X-A^1-A^2-A^3-A^3-A^2-A^1-A^3-A^1-A^3-Y$ | (4) |
| $X-A^1-A^2-A^3-A^2-A^1-A^3-A^3-A^1-A^3-Y$ | (5) |
| $X-A^1-A^2-A^3-A^3-A^2-A^1-A^3-A^2-A^3-Y$ | (6) |
| $X-A^1-A^2-A^3-A^1-A^2-A^3-A^1-A^2-A^3-Y$ | (7) |

$$X\text{-}A^2\text{-}A^1\text{-}A^3\text{-}A^2\text{-}A^1\text{-}A^3\text{-}A^2\text{-}A^1\text{-}A^3\text{-}Y \quad (8)$$

$$X\text{-}A^1\text{-}A^2\text{-}A^3\text{-}A^3\text{-}A^2\text{-}A^3\text{-}A^3\text{-}A^2\text{-}A^1\text{-}Y \quad (9)$$

$$X\text{-}A^1\text{-}A^3\text{-}A^2\text{-}A^3\text{-}A^2\text{-}A^3\text{-}A^2\text{-}A^3\text{-}A^1\text{-}Y \quad (10)$$

$$X\text{-}A^1\text{-}A^2\text{-}A^3\text{-}A^2\text{-}A^1\text{-}A^2\text{-}A^3\text{-}A^2\text{-}A^1\text{-}Y \quad (11)$$

$$X\text{-}A^3\text{-}A^2\text{-}A^3\text{-}A^2\text{-}A^2\text{-}A^3\text{-}A^2\text{-}A^3\text{-}A^3\text{-}Y \quad (12)$$

in which:

X and Y are as defined in claim 1, $A^1$ corresponds to the A group as defined in claim 1, in which R represents an aromatic side chain, $A^2$ corresponds to the A group as defined in claim 1, in which R represents a basic chain corresponding to lysine ($-(CH_2)_4-NH_2$), arginine ($-(CH_2)_3NH-C(=NH)NH_2$) or ornithine ($-(CH_2)_3-NH_2$), or (C1-C10) alkyl, (C1-C10) alkenyl, or (C1-C10) alkynyl, said groups being unsubstituted or substituted by 1 to 6 substituents chosen from: an amidine, $NH_2$, guanidino group, $A^3$ corresponds to the group A as defined in claim 1, in which R represents a hydrophobic side chain of methyl type corresponding to the alanine side chain, isopropyl corresponding to the valine side chain, isobutyl corresponding to the leucine side chain and sec-butyl corresponding to the isoleucine side chain.

3. The compound according to claim 2, which is a compound of one of the following formulae:

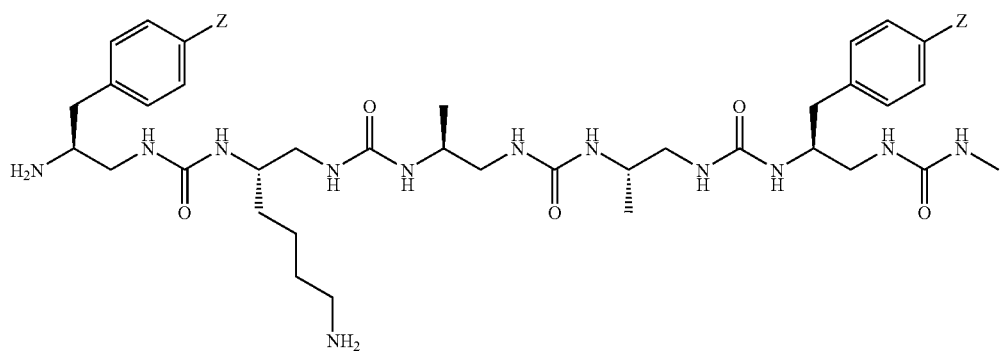

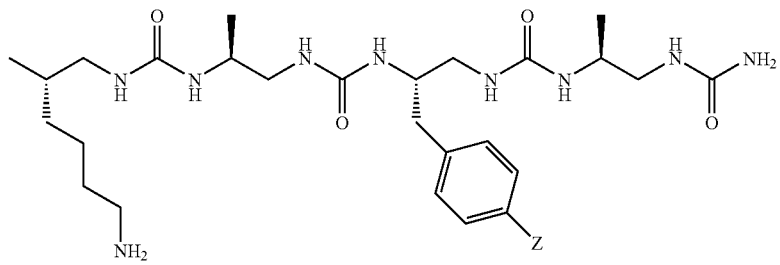

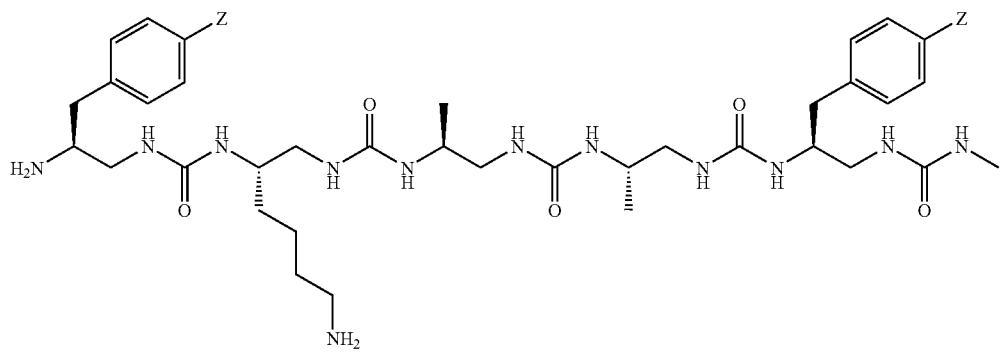

-continued
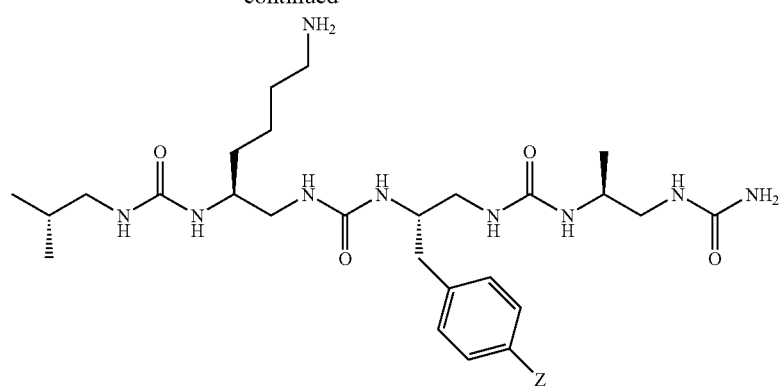
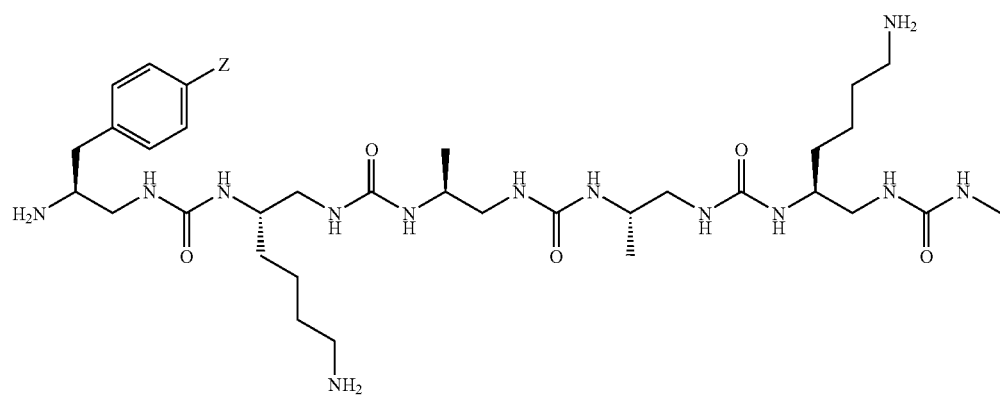
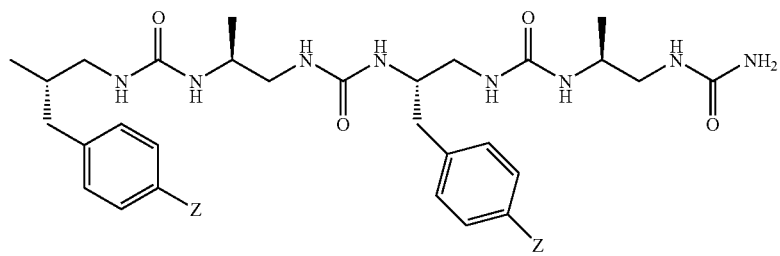
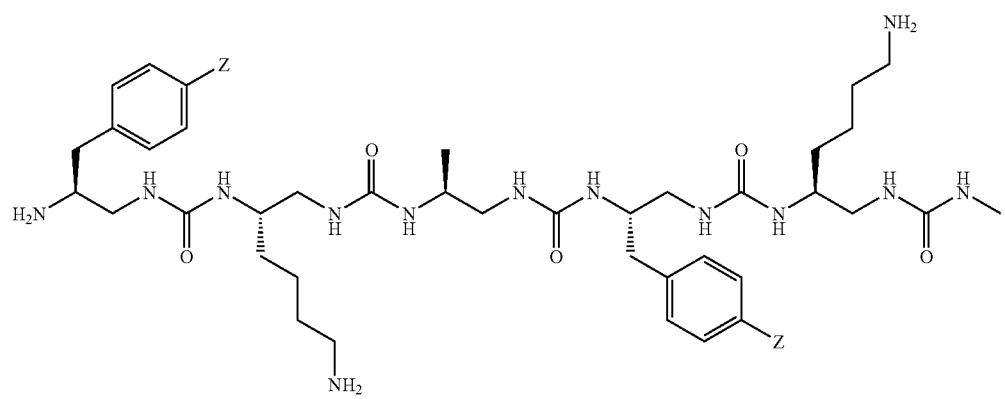

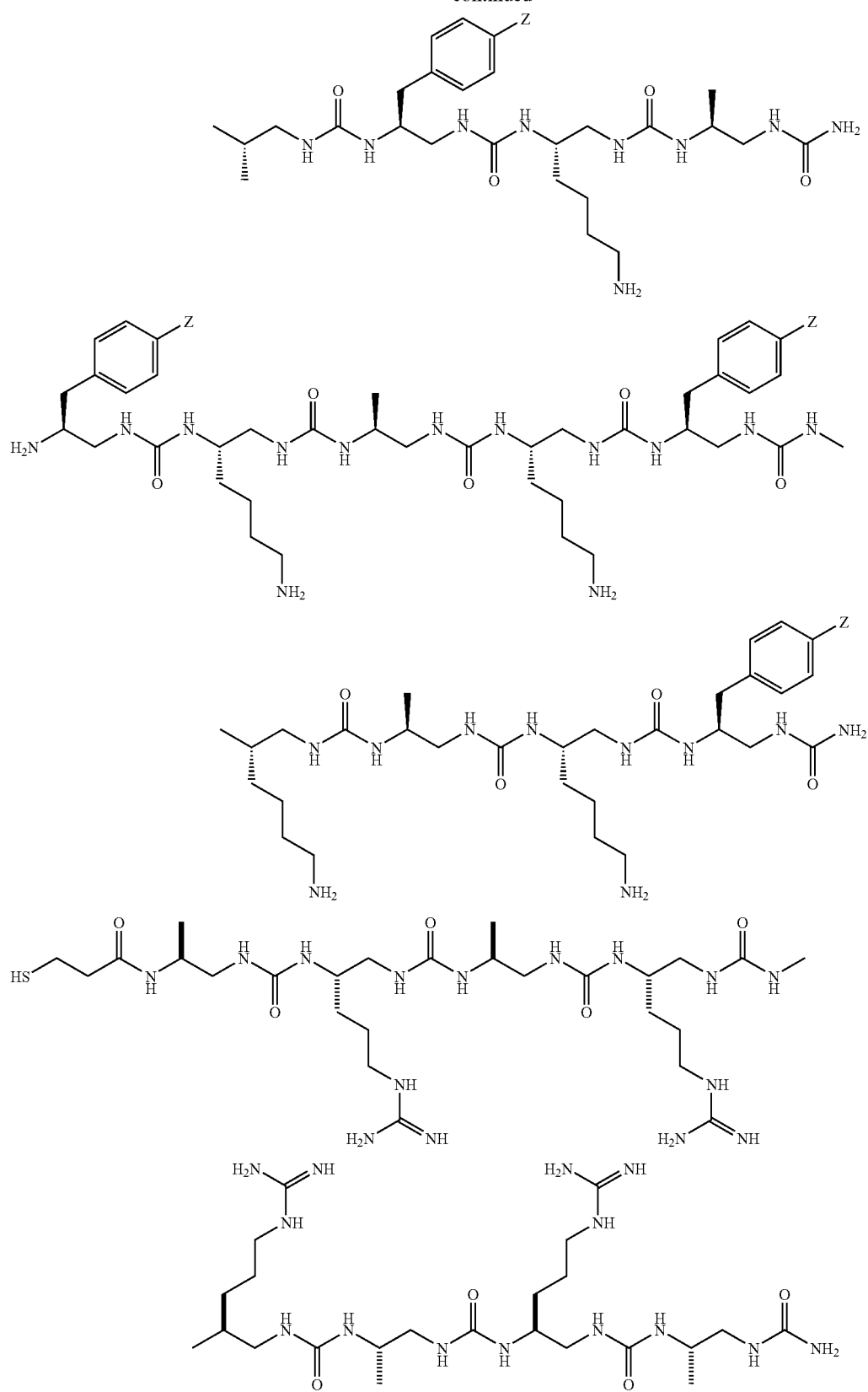

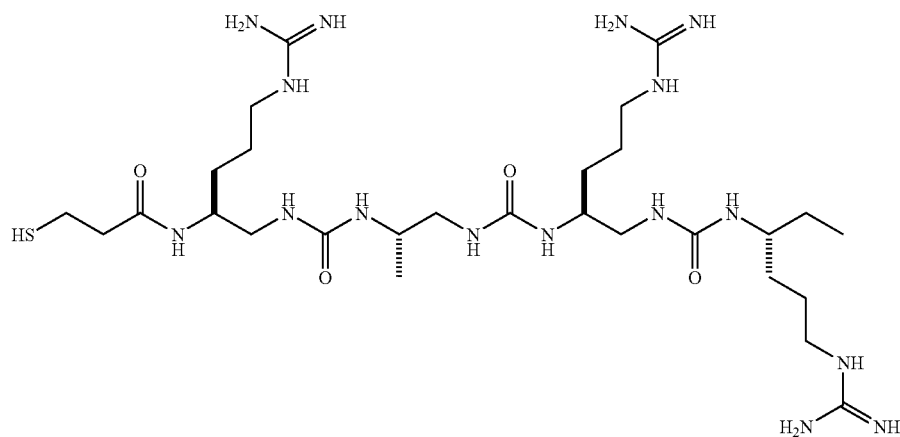
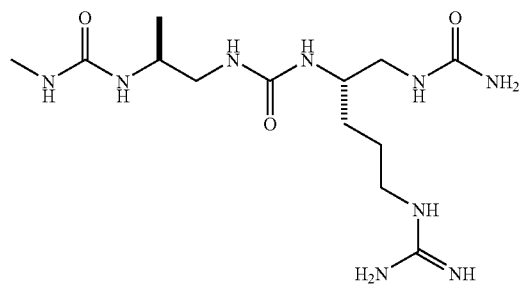
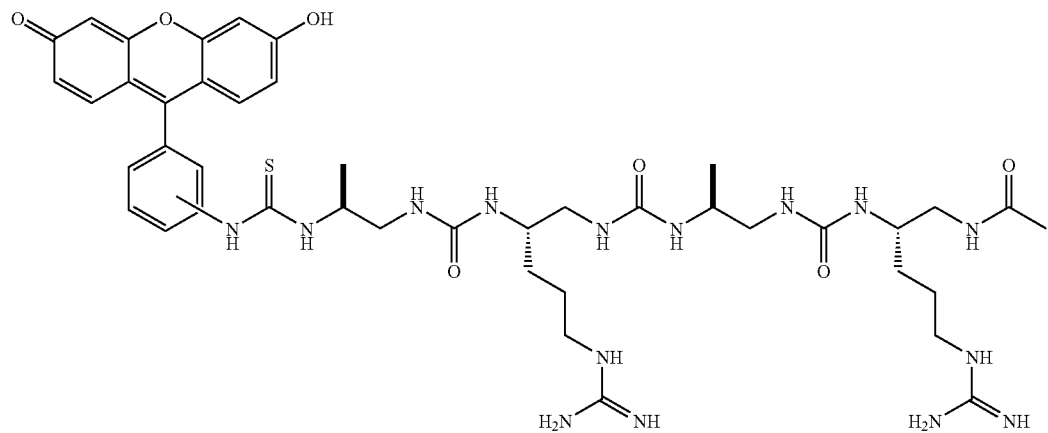
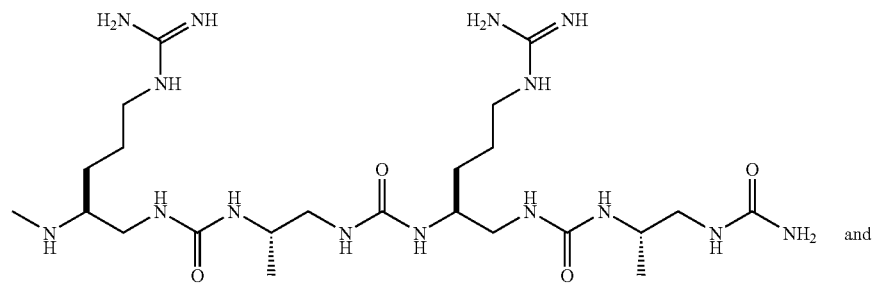 and

-continued

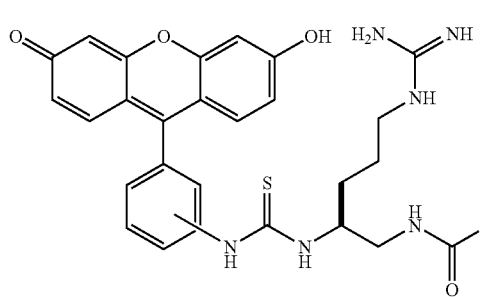
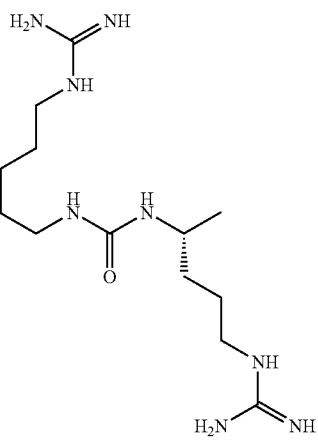

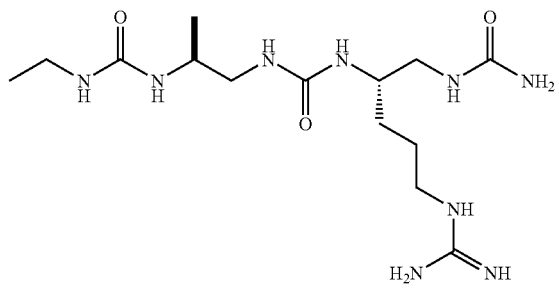

in which Z represents either a hydrogen atom or an OH group.

4. The compound according to claim 1, wherein the amino acid side chains of basic character comprise primary, secondary or tertiary amine groups, imidazole, guanidine, amidine or benzamidine groups.

5. A compound possessing a helical structure and corresponding to the following formula:

$$X—(A)_n—Y, \qquad (I)$$

in which:
  n varies from 6 to 20,
  X represents hydrogen, $R_aCO$, $R_aOCO$, $R_aNHCO$, $R_aSO_2$ or $R_aNHCS$,
    $R_a$ is fluorescein, (C1-C10 alkyl), (C1-C10) alkenyl, (C1-C10) alkynyl, (C5-C12) aryl, (C5-C14) aralkyl, or (C1-C5) heteroaryl, which groups are unsubstituted or substituted by 1 to 6 substituents chosen from: halogen, $NO_2$, OH, (C1-C4) alkyl, $NH_2$, CN, trihalomethyl, (C1-C4) acyloxy, (C1-C4) dialkylamino, guanidino, SH, and maleimide, provided that X is not H when n is 6,
  A represents either:

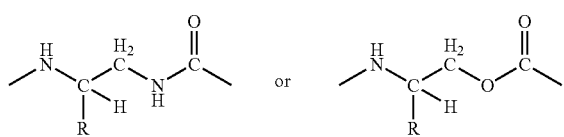

R being hydrogen, an amino acid side chain, (C1-10) alkyl, (C1-10) alkenyl, (C1-10) alkynyl, (C5-12) aryl, (C5-14) aralkyl or (C1-10) heteroaryl, said groups being unsubstituted or substituted by 1 to 6 substituents chosen from: halogen, $NO_2$, OH, amidine, benzamidine, imidazole, alkoxy, (C1-4) alkyl, $NH_2$, CN, trihalomethyl, acyloxy (C1-4), dialkylamino (C1-4), and guanidino, and with the proviso that approximately 10% to approximately 50% of the R substituents are amino acid side chains of basic character, Y is an $NR_bR_c$ group, $R_b$ and $R_c$ having the same meaning as for R, said helix having the following characteristics:
  a regular pitch to the right, comprised from approximately 4.9 Å to approximately 5.3 Å,
  comprises from 2.4 to 2.6 residues per turn and in particular 2.5 residues per turn,
  an internal diameter calculated from the centres of the atoms is comprised from approximately 3.8 Å to approximately 4.6 Å,
  an internal diameter calculated from the Van der Waals surface is comprised from approximately 1.4 Å to approximately 1.8 Å.

6. The compound according to claim 5, wherein said compound has one of the following formulae:

53 54
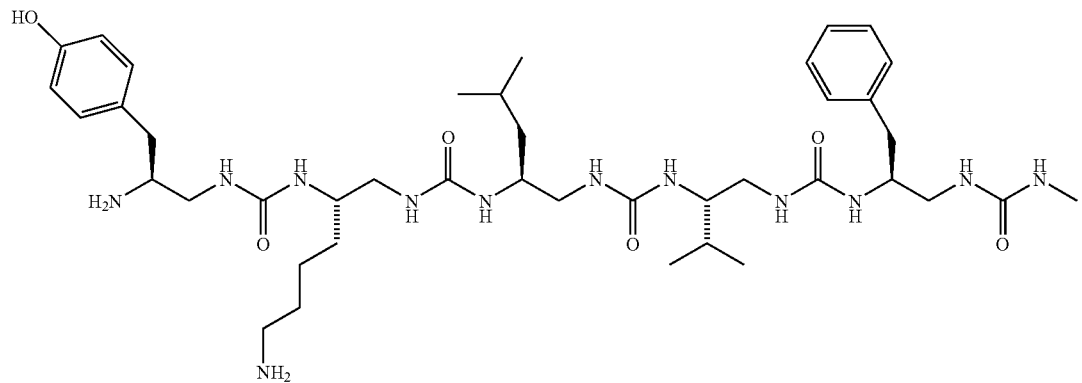
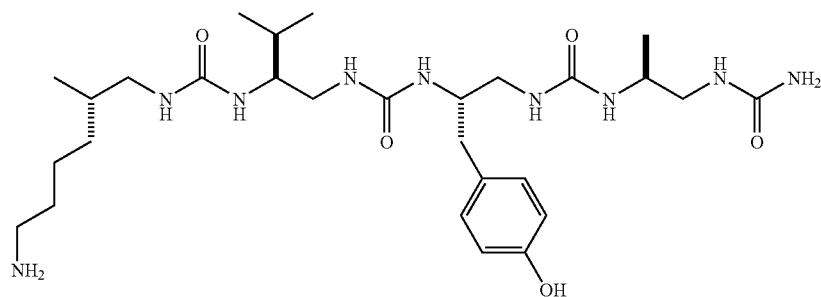
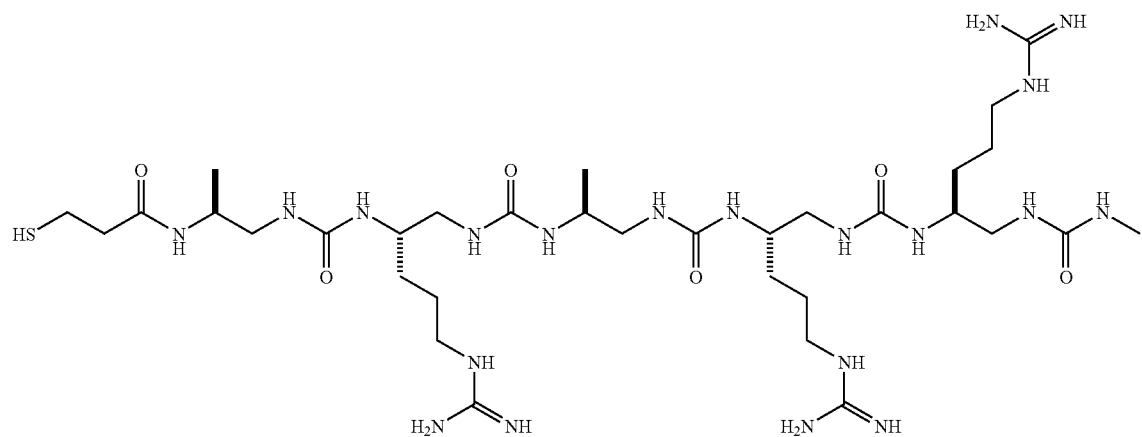
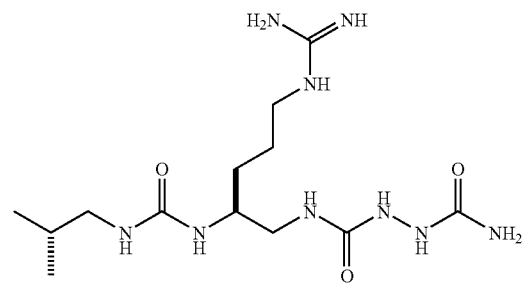

-continued
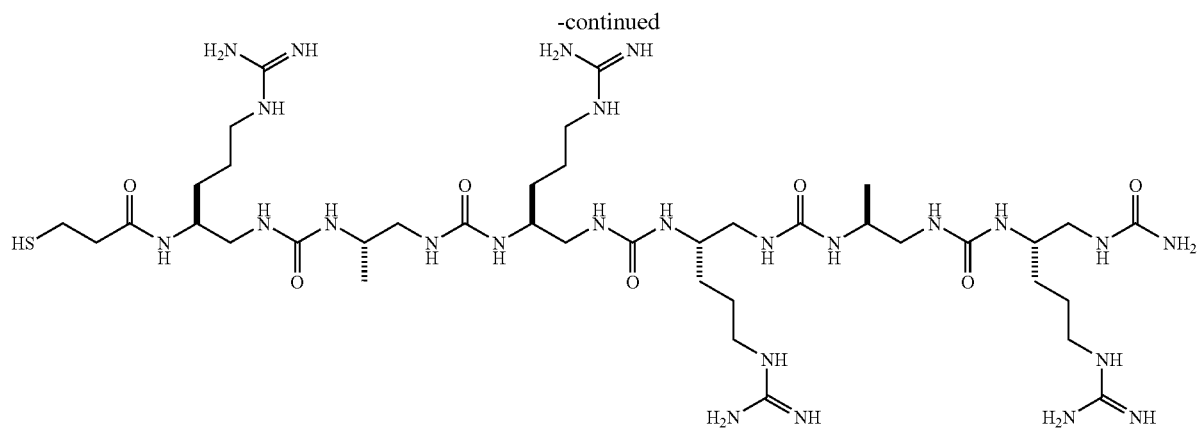
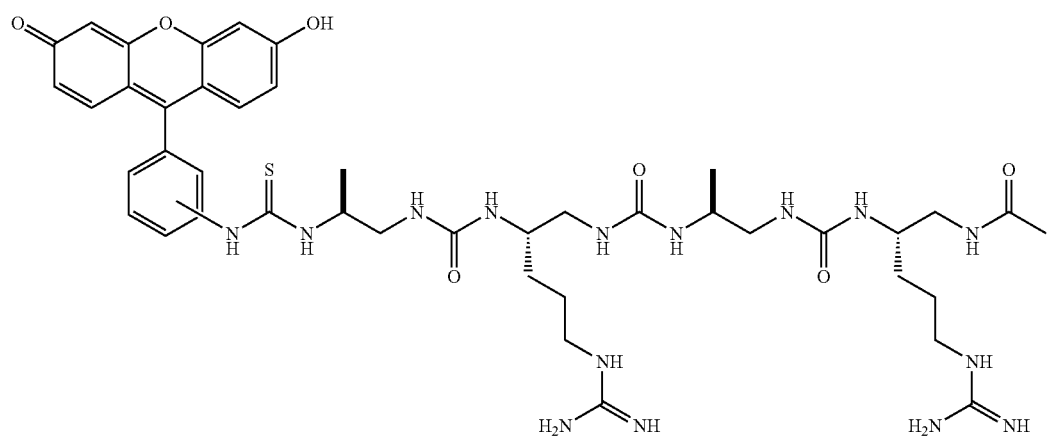
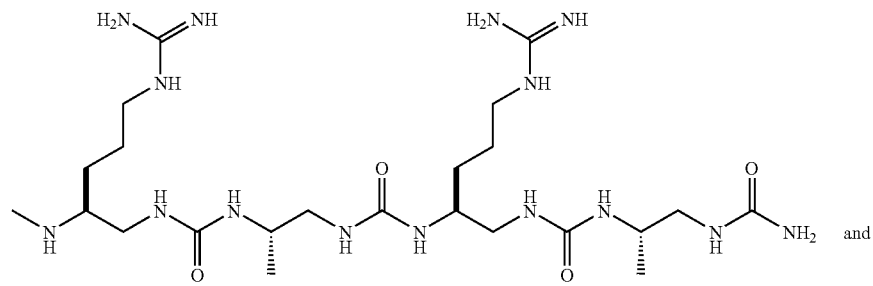 and
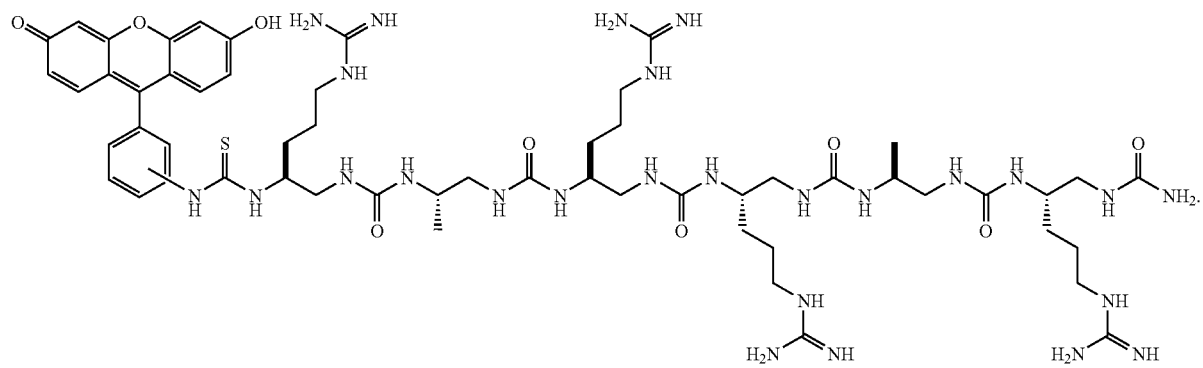

7. A composition comprising at least one compound according to claim 5 and at least one solvent, said solvent having the property of conferring upon the molecules of said compound a helicoidal form, even partially, in the case of a conformational equilibrium between the molecules of said compound in the helicoidal form and the molecules of said compound in the non-helicoidal form.

8. A pharmaceutical composition comprising, as an active ingredient, at least one compound according to claim 2, in combination with a pharmaceutically acceptable vector.

9. The pharmaceutical composition according to claim 8, wherein said composition contains per unit dose from 10 to 2000 mg of said compound.

10. Pharmaceutical composition comprising the compound according to claim 5, in combination with a pharmaceutically acceptable vector.

11. Pharmaceutical composition comprising as pharmaceutical vector at least one compound according to claim 1 in combination with a pharmaceutically active ingredient.

12. A process for the preparation in solid phase compounds of formula (I) according to claim 1, from pre-activated monomers of formula GP-A-W, in which:
   GP is a protective group chosen from Fmoc, Teoc, phtalimide, Alloc, BOC and Cbz,
   A is as defined in claim 1,
   W originates from the W-H group chosen from: N-hydroxysuccinimide, phenol, pentafluorophenol, pentachlorophenol, p-nitrophenol, 2,4-dinitrophenol, 2,4,5-trichlorophenol, 2,4-dichloro-6-nitrophenol, hydroxyl-1,2,3-benzotriazole, 1-oxo-2-hydroxydihydrobenzotriazine (HODhbt), 7-aza-1-hydroxy-benzotriazole (HOAt), 4-aza-1-hydroxybenzo-triazole (4-HOAt), imidazole, tetrazole, and WANG resin,
wherein said process comprises the following stages:
   a) a stage of coupling of GP-A-W as defined above on the amine function of a support, said stage allowing the grafting of the-A-GP group to said amine function of said support,
   b) a cleavage stage of the GP group,
   c) the sequential repetition of stages a) and b) until n A groups have been grafted to said support,
   d) a stage of introduction of the $R_aCO$, $R_aOCO$, $R_aNHCO$ or $R_aSO_2$ groups, $R_a$ being as defined in claim 1, and
   e) a stage of cleavage of the compound of formula (I) from the support, which allows the removal of the resin and the release of the Y group, as defined in claim 1.

13. The process according to claim 12, wherein said stage a) can be carried out in the presence or absence of a tertiary base, and in the presence or absence of a catalyst.

14. The process according to claim 12, wherein said stage a) can be carried out in a solvent selected from the group consisting of DMF, $CH_2Cl_2$, THF and N-methylpyrrolidone.

15. The preparation process according to claim 12, wherein the GP group is an Fmoc group.

16. A process for the preparation in liquid phase of the compounds of formula (I) according to claim 1, from pre-activated monomers of formula GP-A-W, in which:
   GP is a protective group chosen from Fmoc, Alloc, BOC and Cbz,
   A is as defined in claim 1,
   W originates from the W-H group chosen from: N-hydroxysuccinimide, phenol, pentafluorophenol, pentachlorophenol, p-nitrophenol, 2,4-dinitrophenol, 2,4,5-trichlorophenol, 2,4-dichloro-6-nitrophenol, hydroxy-1,2,3-benzotriazole, 1-oxo-2-hydroxydihydrobenzotriazine (HODhbt), 7-aza1-hydroxy-benzotriazole (HOAt), 4-aza-1-hydroxybenzo-triazole (4-HOAt), imidazole and tetrazole,
wherein said process comprises the following stages:
   a) a stage of coupling of GP-A-W as defined above to the amine function of the A group of the H-A-Y derivative,
   b) a stage of cleavage of the GP group,
   c) the sequential repetition of stages a) and b) until n A groups have been grafted to the amine function mentioned above,
   d) a stage of introduction of the $R_aCO$, $R_aOCO$, $R_aNHCO$ or $R_aSO_2$ groups, $R_a$ being as defined in claim 1, and
   e) a stage of cleavage of the compound of formula (I).

* * * * *